United States Patent
Park et al.

(10) Patent No.: US 12,277,866 B2
(45) Date of Patent: Apr. 15, 2025

(54) ORGANOSYNTHETIC DYNAMIC HEART MODEL

(71) Applicants: Massachusetts Institute of Technology, Cambridge, MA (US); The General Hospital Corporation, Boston, MA (US)

(72) Inventors: Clara Park, Cambridge, MA (US); Xuanhe Zhao, Cambridge, MA (US); Hyunwoo Yuk, Cambridge, MA (US); Christopher Tam Nguyen, Cambridge, MA (US); Ellen T. Roche, Cambridge, MA (US)

(73) Assignees: MASSACHUSETTS INSTITUTE OF TECHNOLOGY, Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 1044 days.

(21) Appl. No.: 17/193,910

(22) Filed: Mar. 5, 2021

(65) Prior Publication Data
US 2021/0350725 A1   Nov. 11, 2021

Related U.S. Application Data

(60) Provisional application No. 63/021,014, filed on May 6, 2020.

(51) Int. Cl.
| | |
|---|---|
| G09B 23/30 | (2006.01) |
| G09B 23/32 | (2006.01) |
| B33Y 80/00 | (2015.01) |
| G01N 3/08 | (2006.01) |
| G01N 3/32 | (2006.01) |

(52) U.S. Cl.
CPC ........... *G09B 23/306* (2013.01); *G09B 23/30* (2013.01); *G09B 23/32* (2013.01); *B33Y 80/00* (2014.12); *G01N 3/08* (2013.01); *G01N 3/32* (2013.01); *G01N 2203/0005* (2013.01);
(Continued)

(58) Field of Classification Search
CPC ....... G09B 23/38; G09B 23/30; G09B 23/306
See application file for complete search history.

(56) References Cited

U.S. PATENT DOCUMENTS

| | | | |
|---|---|---|---|
| 7,798,815 B2 | 9/2010 | Ramphal et al. | |
| 10,229,615 B2 | 3/2019 | Carson et al. | |
(Continued)

FOREIGN PATENT DOCUMENTS

WO    2017165969 A1    10/2017

OTHER PUBLICATIONS

Ballester, et al., "The Myocardial Band", Heart Fail. Clin., 4:261-272 (2008).
(Continued)

*Primary Examiner* — Kurt Fernstrom
(74) *Attorney, Agent, or Firm* — PABST PATENT GROUP LLP

(57) ABSTRACT

A biorobotic hybrid heart that preserves organic intracardiac structures and mimics cardiac motion by image-guided replication of the cardiac myofiber architecture of the left ventricle with an active synthetic myocardium that drives the motion of the heart. The active soft tissue mimic is adhered to the organic endocardial tissue in a helical fashion using a custom-designed adhesive to form a flexible, conformable, and watertight organosynthetic interface.

34 Claims, 15 Drawing Sheets

(52) U.S. Cl.
CPC ............... *G01N 2203/0017* (2013.01); *G01N 2203/0062* (2013.01); *G01N 2203/0091* (2013.01)

(56) References Cited

U.S. PATENT DOCUMENTS

| | | | |
|---|---|---|---|
| 11,304,644 B2* | 4/2022 | Lu | A61N 1/08 |
| 11,915,610 B2* | 2/2024 | Fernandez | A01N 1/02 |
| 2019/0272776 A1* | 9/2019 | Fiore | A01N 1/0247 |
| 2020/0286406 A1* | 9/2020 | Alexander | A61B 34/10 |
| 2021/0350725 A1 | 11/2021 | Park et al. | |
| 2022/0064601 A1* | 3/2022 | Mohamed | G01N 33/5082 |
| 2023/0129490 A1 | 4/2023 | Zhou | |

OTHER PUBLICATIONS

Buckberg, et al., "Cardiac Mechanics Revisited: The Relationship of Cardiac Architecture to Ventricular Function", Circulation, 118:2571-87 (2008a).

Buckberg, et al., "Structure and function relationships of the helical ventricular myocardial band", J. Thorac. Cardiovasc. Surg., 136(3):578-89, 589 e1-11 (2008b).

Chu, et al., Engineers design bionic "heart" for testing prosthetic valves, other cardiac devices, MIT News, retrieved from the internet, <https://news.mit.edu/2020/bionic-heart-prosthetic-valve-cardiac-0129>, accessed Jul. 20, 2021.

Edelman, et al., "In vivo measurement of water diffusion in the human heart", Magn. Reson. Med., 32(3):423-8 (1994).

Hinton, et al., "Three-dimensional printing of complex biological structures by freeform reversible embedding of suspended hydrogels", Sci. Adv., 1(9):e1500758, 10 pages (2015).

Horvarth, et al., "Towards Alternative Approaches for Coupling of a Soft Robotic Sleeve to the Heart", Annals of Biomedical Engineering, 46(10):1534-1547 (2018).

Lundberg, et al., "Building a bioartificial heart: Obstacles and opportunities", J. Thorac. Cardiovasc. Surg., 153(4): 748-50 (2017).

MacQueen, et al., "A tissue-engineered scale model of the heart ventricle", Nat. Biomed. Eng., 2(12):930-41 (2018).

Marchese, et al., "Autonomous Soft Robotic Fish Capable of Escape Maneuvers Using Fluidic Elastomer Actuators", Soft Robot., 1(1):75-87 (2014).

Martinez, "Robotic tentacles with three-dimensional mobility based on flexible elastomers", Adv. Mater., 25(2):205-12 (2013).

Moser, et al., "Recellularization of organs: what is the future for solid organ transplantation?", Curr. Opin. Organ Transplant., 19(6):603-9 (2014).

Nguyen, et al., "Diffusion Tensor Cardiac Magnetic Resonance Reveals Exosomes From Cardiosphere-Derived Cells Preserve Myocardial Fiber Architecture After Myocardial Infarction", JACC Basic to Transl. Sci., 3(1):97-109 (2018).

Nguyen, et al., "In vivo diffusion-tensor MRI of the human heart on a 3 tesla clinical scanner: An optimized second order (M2) motion compensated diffusion-preparation approach", Magn. Reson. Med., 76(5):1354-63 (2016).

Park, et al., A Soft Wearable Robotic Device for Active Knee Motions using Flat Pneumatic Artificial Muscles, Proc.—IEEE Int. Conf. Robot. Autom., 4805-4810 (2014).

Park, et al., "Dawn arrives at Ceres: Exploration of a small, volatile-rich world", Science, 353(6303): 1008-1010 (2016).

Park, et al., "An organosynthetic dynamic heart model with enhanced biomimicry guided by cardiac diffusion tensor imaging", Sci. Robot., 5(38):eaay9106, 15 pages (2020).

Pierpaoli, et al., "Toward a quantitative assessment of diffusion anisotropy", Magn. Reson. Med., 36(6): 893-906 (1996).

Poveda, et al., "Helical Structure of the Cardiac Ventricular Anatomy Assessed by Diffusion Tensor Magnetic Resonance Imaging With Multiresolution Tractography", Rev. Esp. Cardiol., 66(10):782-790 (2013).

Reese, et al., "Imaging myocardial fiber architecture in vivo with magnetic resonance", Magn. Reson. Med., 34(6): 786-91 (1995).

Ricotti, et al., "Biohybrid actuators for robotics: A review of devices actuated by living cells", Sci. Robot., 2(12):eaaq0495 (2017).

Roche, et al., "Design and Fabrication of a Soft Robotic Direct Cardiac Compression Device", Proc. ASME Des. Eng. Tech. Conf., 5A, 10 pages (2015).

Roche, et al., "Actuators: A bioinspired soft actuated material", Adv. Mater., 26(8):1200-6 (2014).

Roche, et al., "Soft robotic sleeve supports heart function", Sci. Transl. Med., 9(373):eaaf3925 (2017).

Rus, et al., "Design, fabrication and control of soft robots", Nature, 521:467-75 (2015).

Torrent-Guasp, et al., "The Structure and Function of the Helical Heart and Its Buttress Wrapping. I. The Normal Macroscopic Structure of the Heart", Semin. Thorac. Cardiovasc. Surg., 13(4):301-19 (2001).

Truby, et al., "Printing soft matter in three dimensions", Nature, 540(7633):371-8 (2016).

Wallin, et al., "3D printing of soft robotic systems", Nat. Rev. Mater., 3:84-100 (2018).

Webster-Wood, et al., "Organismal Engineering: Towards a Robotic Taxonomic Key for Devices Using Organic Materials", Sci. Robot., 2(12):eaap9281 (2017).

Wirekoh, et al., "Design of flat pneumatic artificial muscles", Smart Mater. Struct., 26: 035009 (2017).

Yuk, et al., "Dry double-sided tape for adhesion of wet tissues and devices", Nature, 575(7781):169-174 (2019).

Zhang, et al., "3D Bioprinting for Tissue and Organ Fabrication", Ann. Biomed. Eng., 45(1):148-63 (2017).

International Search Report for PCT/US2021/030805 dated Aug. 6, 2021.

International Search Report received for PCT Patent Application No. PCT/US2024/028128, mailed on Aug. 20, 2024, 4 pages.

* cited by examiner

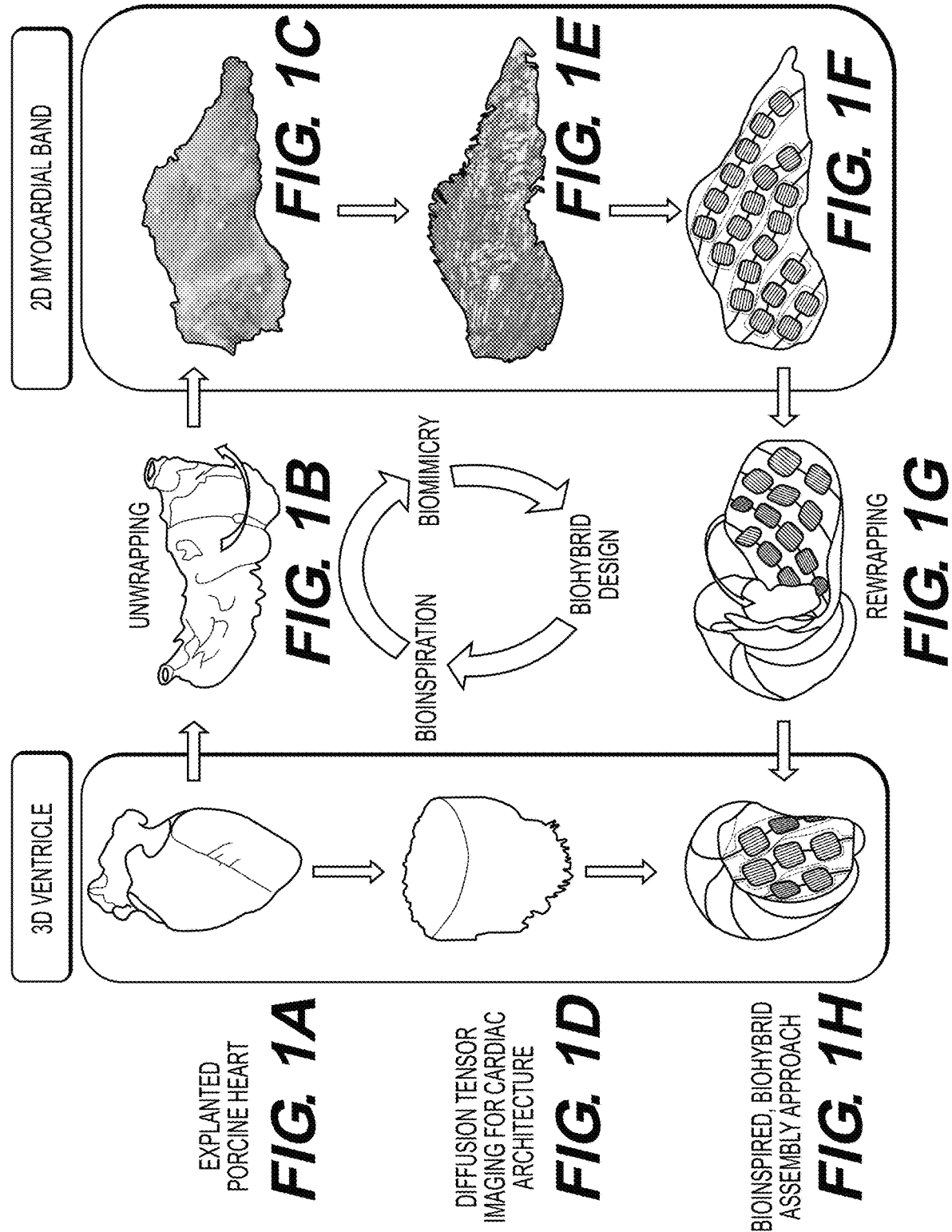

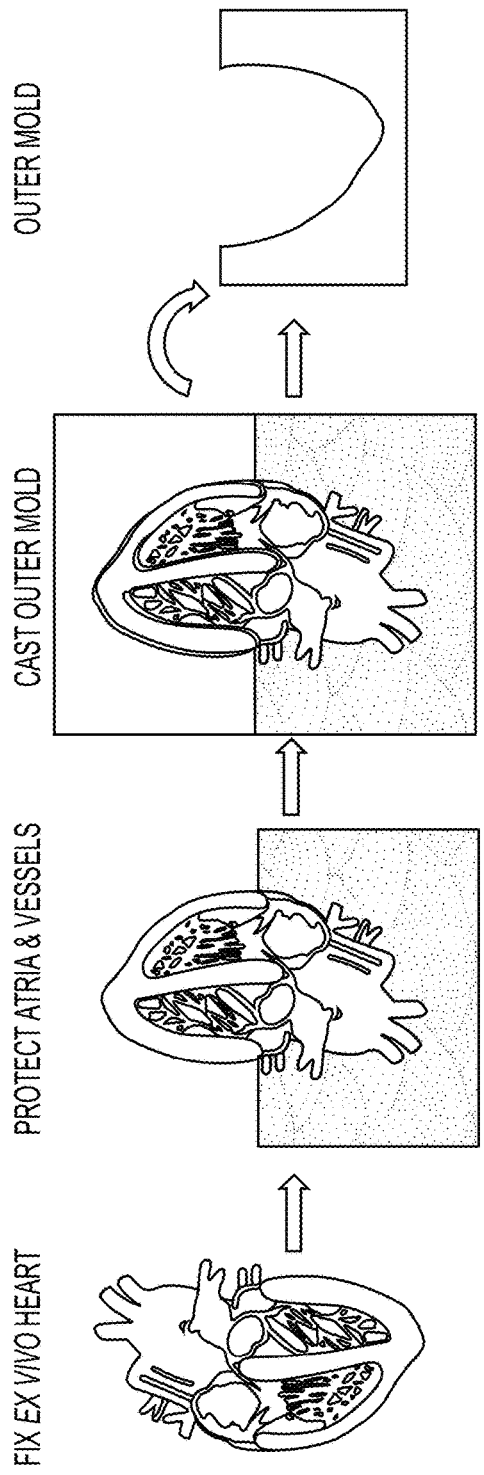
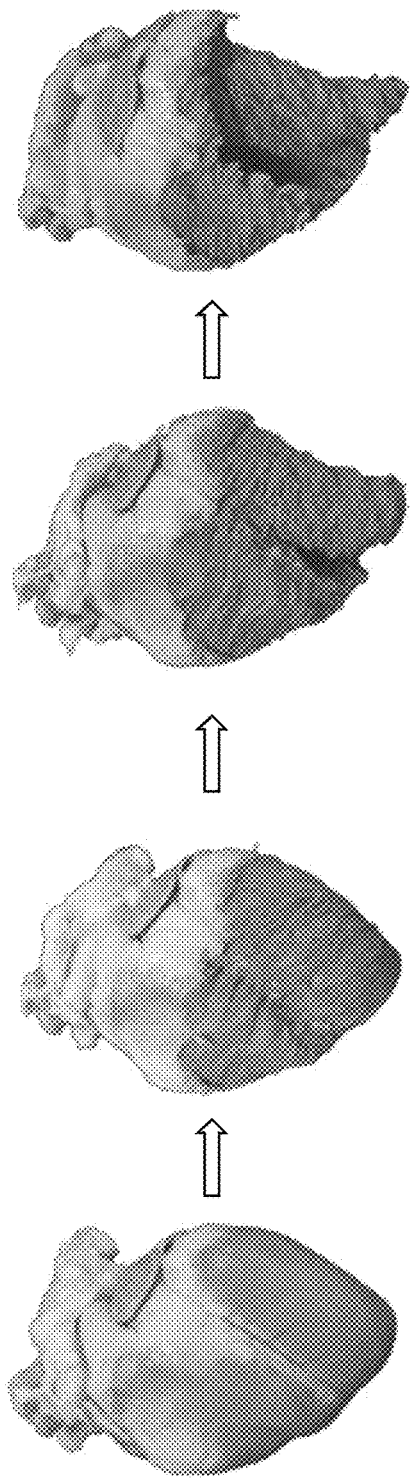

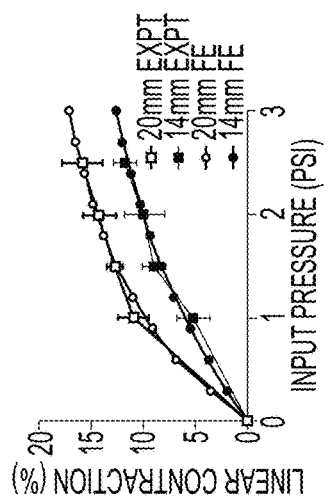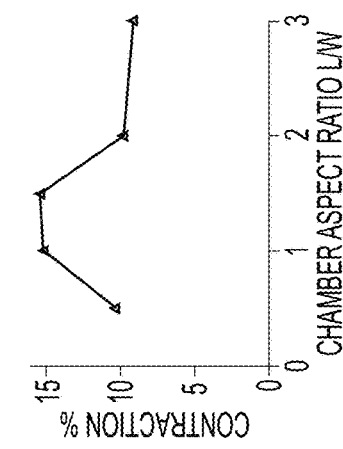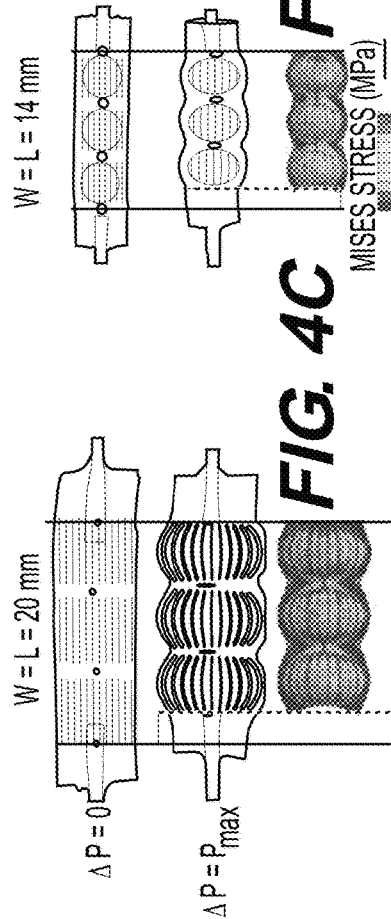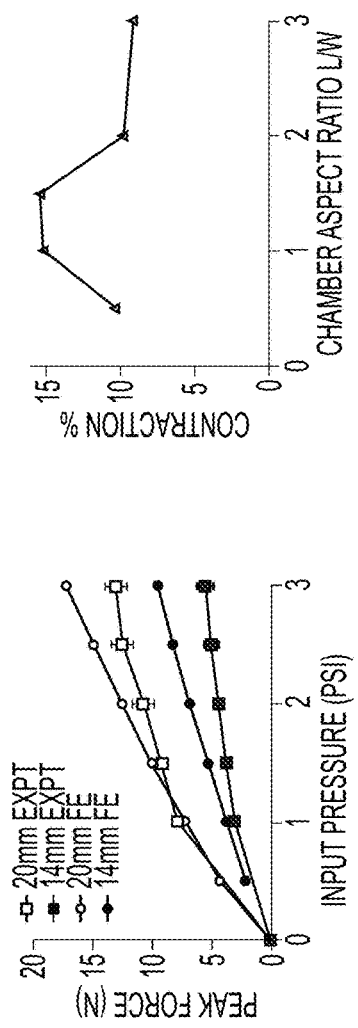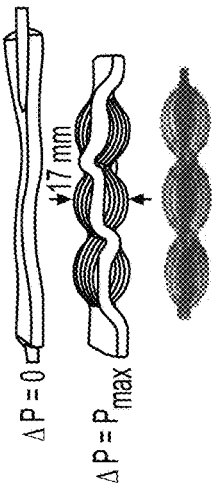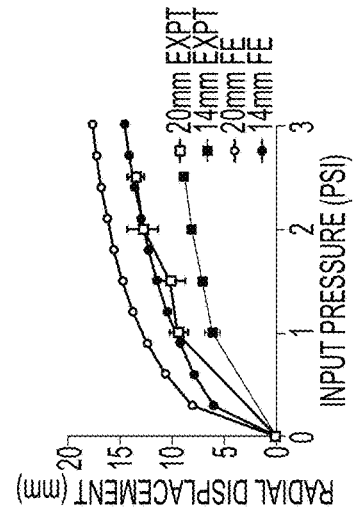

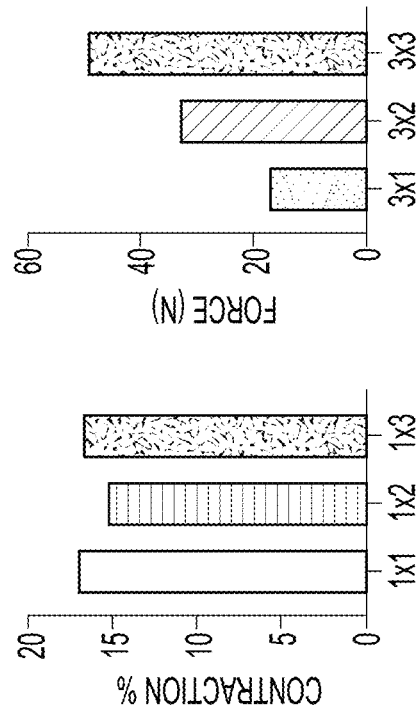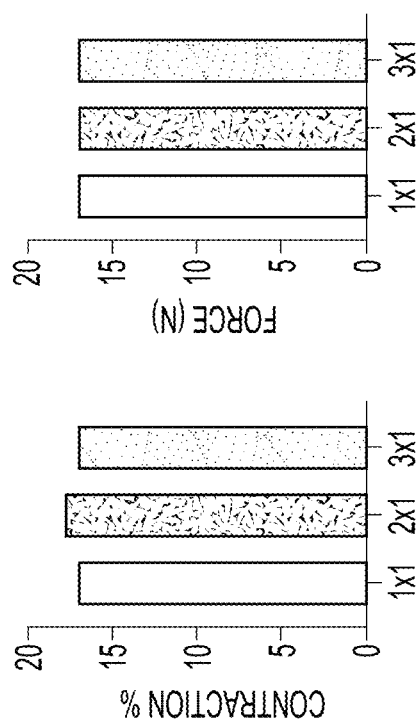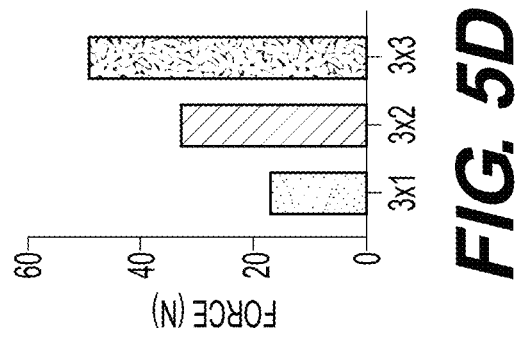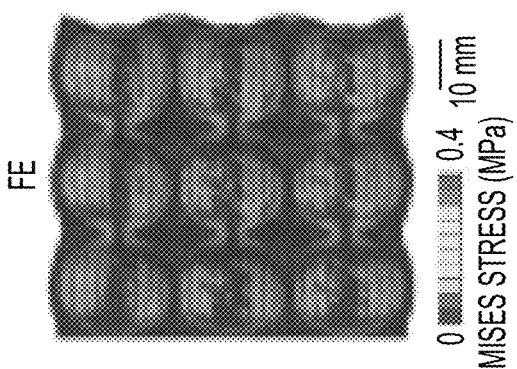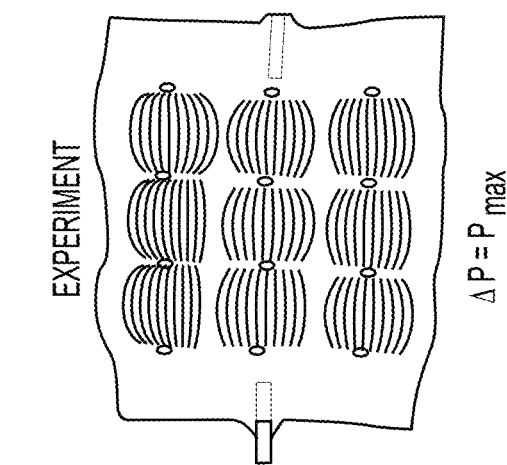
FIG. 5A  FIG. 5B  FIG. 5C  FIG. 5D  FIG. 5E  FIG. 5F

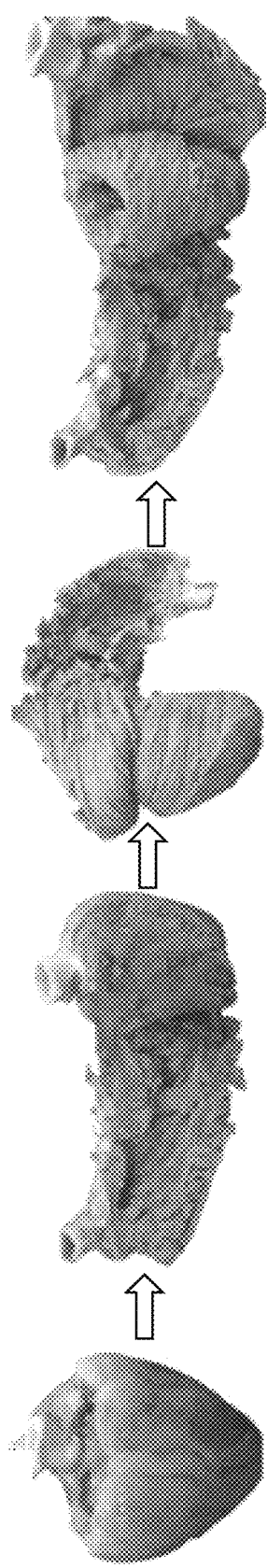
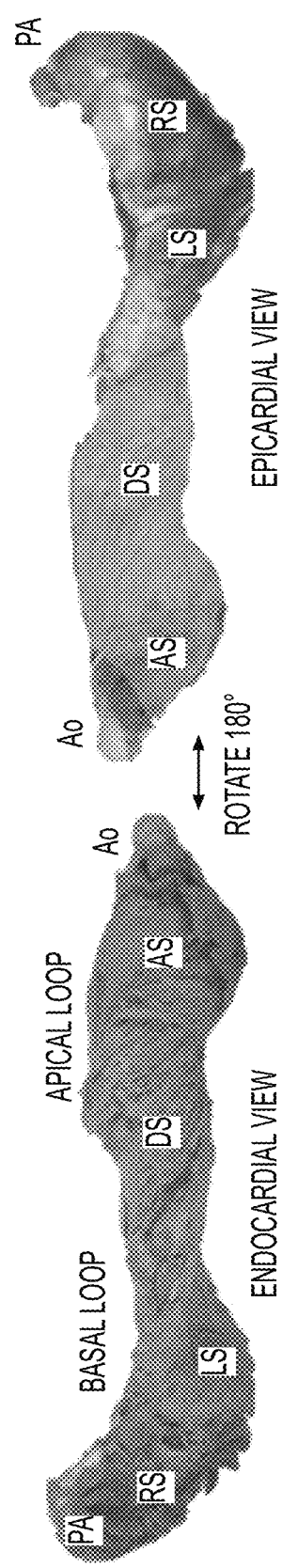
FIG. 6A  FIG. 6B  FIG. 6C  FIG. 6D
FIG. 6E  FIG. 6F

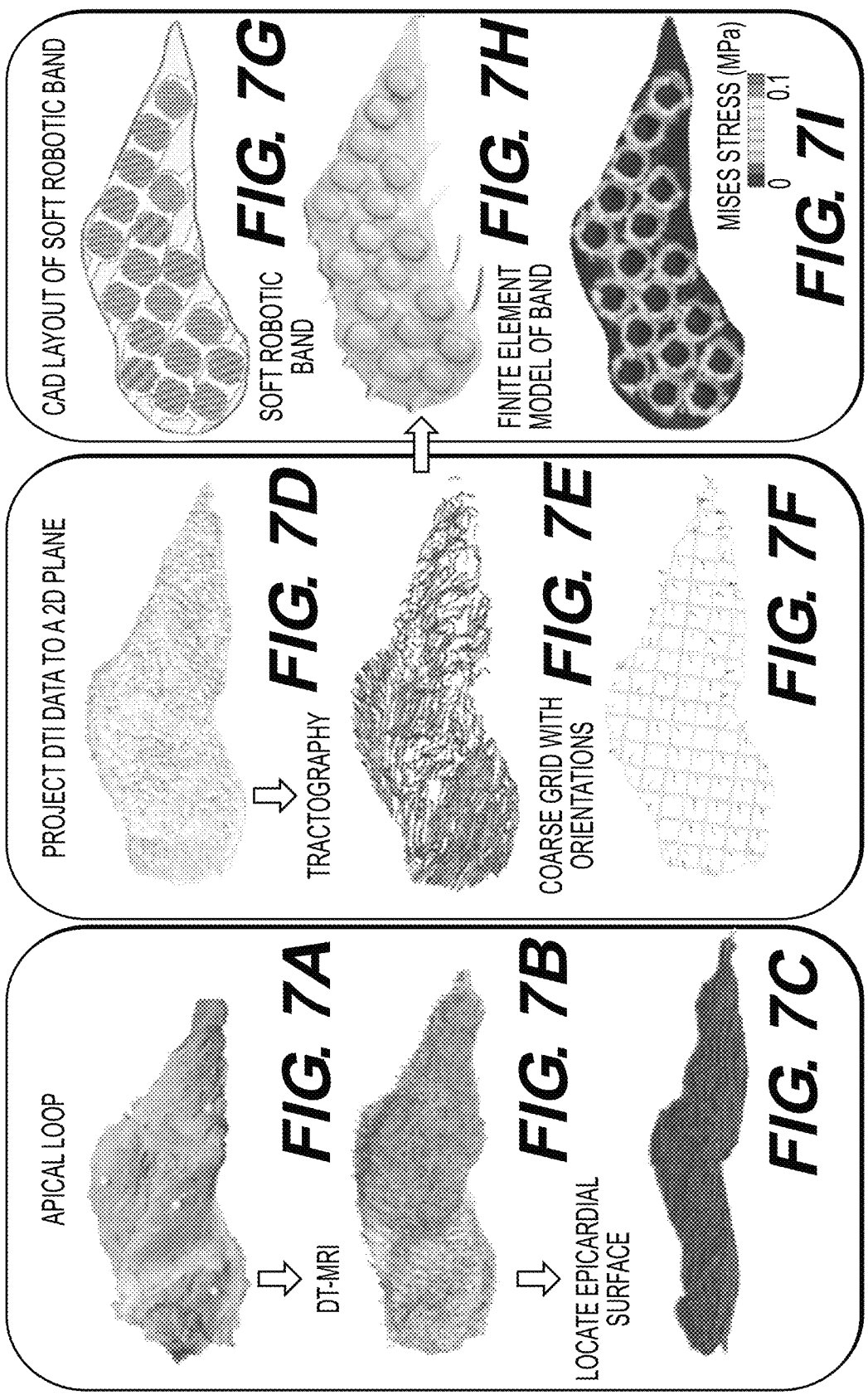

ORGANOSYNTHETIC DYNAMIC HEART MODEL

CROSS REFERENCE TO RELATED APPLICATIONS

This application claims the benefit of and priority to U.S. Provisional Application No. 63/021,014, filed May 6, 2020, and is hereby incorporated herein by reference in its entirety.

STATEMENT REGARDING FEDERALLY SPONSORED RESEARCH

This invention was made with government support under 1847541 awarded by the National Science Foundation and R21EB024701 awarded by the National Institutes of Health. The government has certain rights in the invention.

FIELD OF THE INVENTION

The present invention is generally in the field of artificial hearts and tissue engineering, and more specifically a biohybrid soft robotic heart mimicking myocardial architecture and motion whilst preserving explanted intracardiac structures.

BACKGROUND OF THE INVENTION

There is an unmet clinical need for a high-fidelity benchtop cardiac model for device testing, interventional training, and procedure demonstration. Currently, in most in vitro cardiac simulators, the heart is represented by entirely synthetic or entirely organic components. While synthetic hearts, which are typically silicone- or urethane-based anatomical models, have utility for well-regulated, repeatable experimental conditions, their biofidelity is limited owing to a lack of correct intracardiac anatomical details necessary for evaluating the function, and simulating the placement of intracardiac devices, such as transcatheter valve replacements or occluder devices. Although a realistic representation of cardiac anatomy is achievable by using ex vivo beating heart model, the set-up process can be long and tedious, and the ex vivo heart tissue has limited longevity (<1 day) due to muscle stiffening and decay. Owing to these drawbacks, in vivo animal models are commonly used in industry to test the mechanical performance of intracardiac devices, involving significant experimental cost and time.

The heart is a uniquely challenging organ to recreate due to its dynamic three-dimensional motion and its complex internal cardiac structures. Engineering approaches to making realistic beating heart models include the use of soft robotics and tissue engineering. Recent advances in soft robotics have demonstrated success in replicating complex biological motions at the macroscale (Roche, et al. *Adv. Mater.* 26, 1200-6 (2014); Roche, et al. *Proc. ASME Des. Eng. Tech. Conf.* 5A, 2015; Marchese, et al. *Soft Robot.* 1, 75-87 (2014); Martinez, *Adv. Mater.* 25, 205-12 (2013); Rus et al. *Nature.* 521, 467-75 (2015)). Roche et al. 2015 demonstrated physiological cardiac motion by programming linear pneumatic artificial muscles (PAMs) in a soft matrix. This simplified cardiac simulator, however, lacks anatomical intracardiac structures (such as papillary muscles, chordae tendineae, ventricular trabeculae, valves and moderator bands). These features are challenging to implement with currently available synthetic materials and manufacturing methods at the submillimeter resolution (Truby et al. *Nature.* 540, 371-8 (2016); Wallin, et al. *Nat. Rev. Mater.* 3, 84-100 (2018)).

Entirely biological approaches to recreating the heart in the field of cardiac tissue engineering range from using induced pluripotent stem cells (Macqueen, et al. *Nat. Biomed. Eng.* 2, 930-41 (2018)), bioprinting cell-seeded artificial scaffolds (Zhang, et al. *Ann. Biomed. Eng.* 45, 148-63 (2017; Hinton, et al. *Sci. Adv.* 1, (2015)) to decellularized heart tissues (Moser, et al. *Curr. Opin. Organ Transplant.* 19, 603-9 (2014)). However, currently, there is no functional bioartificial heart at the human organ scale. There are remaining challenges in scaling up tissue-engineered constructs due to difficulties in obtaining cells and sustaining tissue vascularization and viability (Lundberg, et al. *J. Thorac. Cardiovasc. Surg.* 153, 748-50 (2017)), as well as in achieving the contractile function at a physiological level even at the microscale. Furthermore, the use of viable biological tissues requires the maintenance of sterile culture conditions at all times, making it impractical for benchtop testing.

It is therefore an object of the present invention to provide a functional alternative to tissue based or synthetic material based heart mimicking devices.

SUMMARY OF THE INVENTION

A biorobotic hybrid heart that preserves organic intracardiac structures and mimics cardiac motion by replicating the cardiac myofiber architecture of the left ventricle is composed of organic endocardial tissue from a preserved explanted heart with intact intracardiac structures, and an active synthetic myocardium that drives the motion of the heart. Inspired by the helical ventricular myocardial band theory, diffusion tensor magnetic resonance imaging and tractography of an unraveled organic myocardial band is used to guide the design of individual soft robotic actuators in a synthetic myocardial band. The active soft tissue mimic is adhered to the organic endocardial tissue in a helical fashion using a custom-designed adhesive to form a flexible, conformable, and watertight organosynthetic interface. Heart tissues of all forms, not just limited to chemically preserved heart, including biological tissue, chemically preserved or decellularized matrix that retain internal structures of the heart, can be used.

The resulting biorobotic hybrid heart simulates the contractile motion of the native heart, compared to in vivo and in silico heart models, thereby recapitulating both the complex motion and anatomical features of the heart. As demonstrated by the example, endocardial (inner heart) tissue directly from a porcine heart is used to accurately represent the anatomical details of intracardiac structures while soft robotic techniques are utilized to recreate the dynamic cardiac motion. The heart tissue is chemically fixed to enhance longevity for benchtop settings. By utilizing soft robotic techniques to replicate physiological motion and merging this technology with organic tissue, this biohybrid heart model overcomes both the scalability limitations in tissue engineering, and the challenges in recreation of fine structural details with conventional manufacturing technology.

The complex motion of the beating heart is accomplished by the spatial arrangement of contracting cardiomyocytes with varying orientation across the transmural layers, which is difficult to imitate in organic or synthetic models. High-fidelity testing of intracardiac devices requires anthropomorphic, dynamic cardiac models that represent this complex motion, whilst maintaining the intricate anatomical structures inside the heart.

In some embodiments, the biohybrid heart includes heart valve leaflets and the attached chordae from an explanted heart as the endocardial tissue scaffold to represent relevant intracardiac anatomy and material properties for particular applications, such as valve prosthetic device testing, and optionally other intracardiac components formed of synthetic materials, such as the inner ventricular wall). Preferred synthetic materials include 3D printed elastomers.

A method for constructing a biohybrid heart that consists of an ex vivo endocardial tissue scaffold and synthetic myocardium was developed in this process, as well as a new soft tissue-silicone adhesive referred to as TISSUESIL to allow coupling of the organic endocardium and synthetic myocardium, as existing adhesives suffer from critical drawbacks, such as weak adhesion (e.g., PEG- or fibrin-based adhesives) between tissue and silicone, mechanical mismatch with soft tissues, brittleness, and incompatibility in wet environment (e.g., cyanoacrylates). The tissue adhesive forms a reliable organosynthetic interface while handling large deformations in wet conditions. The adhesive contains the moiety:

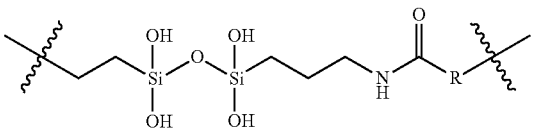

wherein, R is NH, O, or S, optionally wherein the termini are connected to a polymeric substrate (PDMS) or tissue A flat soft robotic matrix that contains an array of PAMs whose fine fiber reinforcement which can be oriented to match the native heart tissue anisotropy was also developed which overcomes the problems of PAMs used by Roche, et al (2014) and Roche, et al. *Sci. Transl. Med.* 9, eaaf3925 (2017), which occupy high dead volume in unactuated state, limiting the number of actuators that can fit in confined space, such as the ventricular myocardium geometry. For enhanced biomimicry, flat pleated PAMs (fPAMs) (Park, et al. *Proc.—IEEE Int. Conf. Robot. Autom.* 4805-10 (2014); Wirekoh, et al. *Smart Mater. Struct.* 26, (2017)) were used with zero-volume air cavities in the unpressurized state, to increase actuator multiplexity and resolution. An fPAM matrix can be manufactured by a one-step fabrication process for a high degree of actuator multiplexity and seamlessly integrated into a soft tissue-mimicking material.

A method for translating high-resolution cardiac myofiber orientation architecture to soft robotic structures using diffusion tensor magnetic resonance imaging (DT-MRI), a non-destructive technique that reveals fiber architecture by detecting anisotropic diffusion of water in tissue (Pierpaoli, et al. *Magn. Reson. Med.* 36, 893-906 (1996); Edelman, et al. *Magn. Reson. Med.* 32, 423-8 (1994); Reese, et al. *Magn. Reson. Med.* 34, 786-91 (1995)), is used with the biohybrid heart model.

This combination of technologies yields a platform for a dynamic heart model that is durable, anatomically accurate, and can recapitulate physiological motion, and can be used as a high-fidelity cardiac benchtop model for the development of intracardiac devices, potentially reducing the overall number of animals used in preclinical and regulatory testing.

BRIEF DESCRIPTION OF THE DRAWINGS

FIGS. 1A-1H are schematics of the process of making a biorobotic hybrid heart. An explanted porcine heart tissue (FIG. 1A) is dissected and unraveled (FIG. 1B) to form a flat, helical ventricular myocardial band (FIG. 1C). Diffusion tensor magnetic resonance imaging of the intact and unraveled heart (FIG. 1D) is used to guide the development of a synthetic myocardial substitute (FIG. 1E). A 2D active band (FIG. 1F) is designed based on the unraveled heart cardiomyocyte orientation. The band is rewrapped (FIG. 1G) around a preserved heart without myocardium (FIG. 1H), and the organic and synthetic structures were coupled to form a biorobotic hybrid heart.

FIGS. 2A-2L are schematics of the fabrication process for a passive biohybrid heart. FIGS. 2A-2D show casting of the outer mold: An explanted porcine heart (FIG. 2A) is preserved and the superior portion is placed in sulfur-free clay (FIG. 2B). The epicardial surface of the ventricular portion of the heart is then cast with MOLDSTAR® 15 (FIG. 2C) to yield the mold (FIG. 2D). FIGS. 2E-2H show the preserved heart dissected in a layer-wise fashion following the cardiomyocyte orientation in the left ventricle. FIGS. 2I-2L show the passive biohybrid heart being cast by centering the dissected heart in the outer mold using supporting struts (FIG. 2I). ECOFLEX® 00-20 is used for casting. Once cured, the assembly is demolded and disassembled (FIG. 2J). Next, tissue-silicone adhesive (TISSUESIL) is applied to the outer tissue surface (FIG. 2K) to yield the final product (FIG. 2L)

FIGS. 3A-3C shows Uniaxial tensile testing of samples of tissue coated with adhesive. Inset in FIG. 3A shows cracking of cyanoacrylate (CA) and co-stretching of TISSUESIL during tensile loading. FIGS. 3M-3O shows burst pressure testing. Data shows mean±SD (n=3). *p<0.05 using one-way ANOVA with post-hoc Tukey test.

FIGS. 4A-4J shows the fabrication and mechanical and computational characterization of single-array fPAMs. FIGS. 4A and 4B show the fabrication process for fPAMs. FIGS. 4C-4E shows a comparison of linear contraction (n=5 for 20 mm×20 mm, n=4 for 14 mm×14 mm) and FIGS. 4F-4H show the radial displacement (n=3) measured experimentally and predicted computationally at P=ΔPmax. FIG. 4I is a graph of the force generation for increasing input pressures measured experimentally (n=6) and predicted computationally. FIG. 4J is a graph of the computational prediction of percentage linear contraction for various aspect ratios (L/W). Data are mean±S.D. L=length of bladder, W=width of bladder, P=actuation input pressure. ΔPmax=2.5 psi. FE=finite element.

FIGS. 5A-5J are the characterization of multiple-array matrices of soft robotic cardiac muscles. FIGS. 5A and 5B are graphs of the FE prediction of contraction percentage and force generation of serial arrays (1×1, 2×1, 3×1). FIGS. 5C and 5D are graphs of the modeling of contraction percentage (1×1, 1×2 and 1×3) and force generation (3×1, 3×2, 3×3) of parallel arrays. FIGS. 5E and 5F show the contraction of a 3×3 array experimentally (FIG. 5E) and computationally (FIG. 5F) at ΔPmax. The contour plot shows Mises stresses in the FE simulation. The graph shows percentage contraction at different input pressures (bottom). FIG. 5G is a graph of the FE prediction of contraction for different actuator spacing in an array. FIGS. 5H and 5I show the inner area reduction of a circumferentially oriented single array with increasing pressure. FIG. 5J is a graph of the uninflated and FIG. 5K is a graph of the inflated state at ΔPmax. ΔPmax=2.5 psi. Data are mean±S.D. n=3.

FIGS. 6A-6F show the inspiration and design process for soft robotic myocardial band. FIGS. 6A-6D shows the unraveling of the helical ventricular myocardial band, and FIGS. 6E and 6F show the resulting product (endocardial view, epicardial view). PA=pulmonary artery, Ao=aorta, RS=right segment, LS=left segment, DS=descending segment, AS=ascending segment.

FIGS. 7A-7I are illustrations of the bioinspired process of fabricating the synthetic band. FIGS. 7A, 7B, 7C, show isolation of the left ventricular band, DT-MRI image data and process of locating the epicardial surface. FIGS. 7D, 7E, 7F are projections of DTI data at epicardial surface onto a 2D plane, tractography data and a coarser grid with principal orientations. FIGS. 7G, 7H, 7I show Computer Aided Design model of bioinspired band, the physical soft robotic myocardial band and the Mises stress contour plot from the finite element model of the actuated band at ΔPmax. DT-MRI=diffusion tensor magnetic resonance imaging.

DETAILED DESCRIPTION OF THE INVENTION

I. Definitions

Figures 2I, 2J, 2K, 2L:
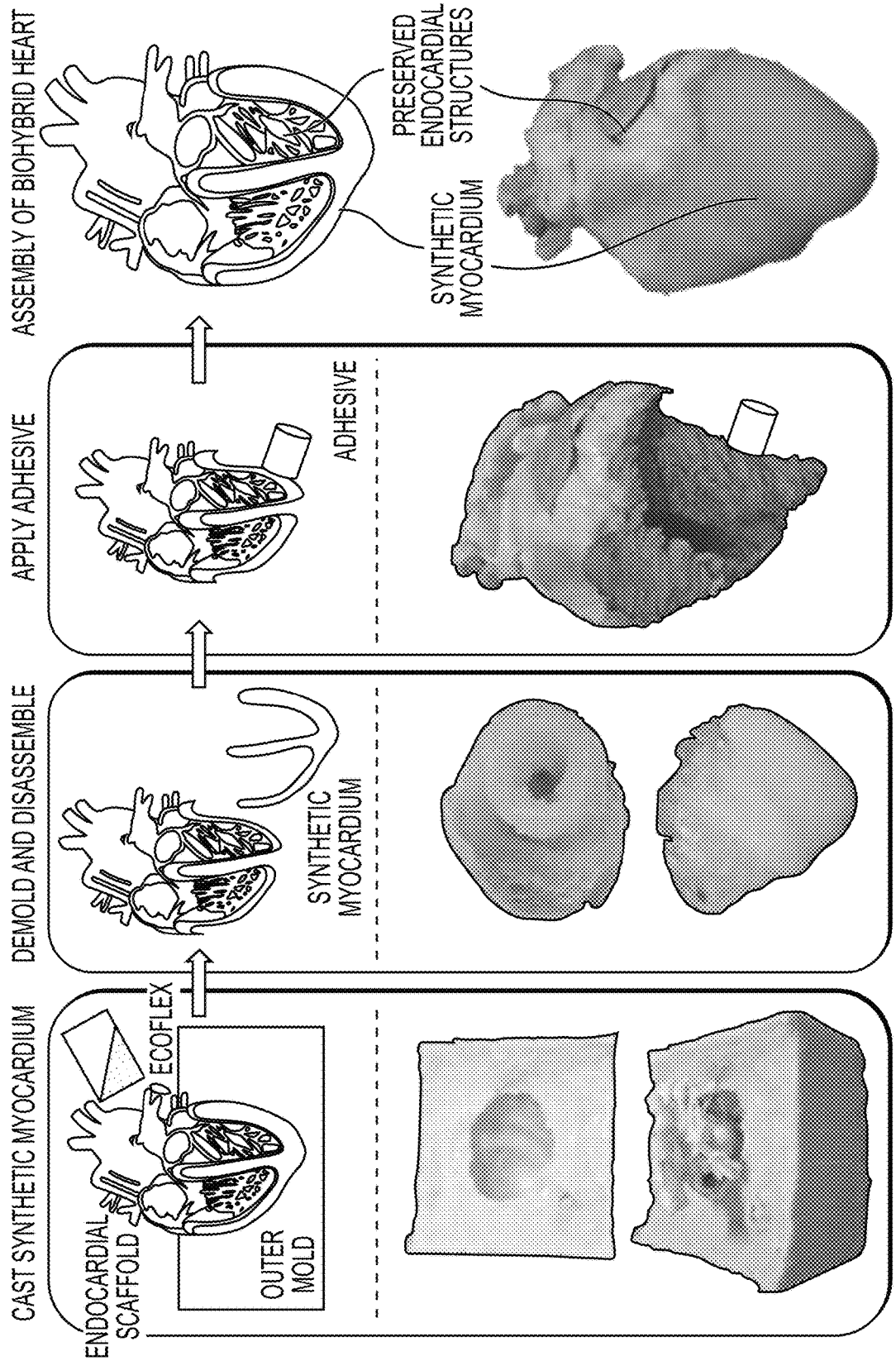

As used herein, "Biohybrid" refers to a device: containing or composed of both biological and non-biological components, such as possessing a component of biological origin; containing biomaterial and non-biological biomaterial; and/or integrating synthetic material with animal (e.g., human) tissue (such as muscles, nerves, or bone).

As used herein, "intracardiac" refers to situated within, occurring within, introduced into, or involving entry into the heart, such as intracardiac surgery using an intracardiac catheter.

As used herein, "endocardial tissue scaffold" refers to the whole heart with removed ventricular myocardial tissues and including intact intracardiac structures, and/or other heart structures such as the atria and major vessels. This includes heart tissues of all forms, not just limited to chemically preserved heart tissues, including biological tissue, chemically preserved or decellularized matrix that retain internal structures of the heart.

As used herein, "synthetic myocardium" refers to cardiac muscle tissue-mimic or -substitute made out of soft synthetic matrix and/or containing actuatable components, such as pneumatic artificial muscles.

As used herein, "soft" refers to material mechanical properties with low modulus similar to most biological tissues in the range of 10 kPa to 10 MPa.

As used herein, "biorobotic hybrid" refer to devices containing or composed of passive biological structures combined with active synthetic materials that can be actuated to produce motion and forces.

As used herein, physiological hemodynamics means development of intraventricular pressures simultaneously with the reduction of ventricular volumes induced by the robotic actuation of the synthetic myocardium (i.e. high pressure/low volume as opposed to high pressure/high volume).

As used herein, "complex three-dimensional cardiac motion" and "physiological level of contractile motion" refer to three-dimensional contraction of the synthetic myocardium, resulting in the reduction of volume/volumes in one or more of the ventricular chambers (which may be left or right only).

II. Biohybrid Heart Model Device

A biohybrid heart has been developed which mimics the intricate arrangements of cardiac fibers. The native myocardium (heart muscle) is composed of layers of individual cardiomyocyte fibers that synchronously contract along their transmurally varying orientations, constituting hierarchical three-dimensional ("3D") structures. Instead of replicating the complex three dimensional fiber structures, the helical ventricular myocardial band (HVMB) theory (Torrent-Guasp, et al. *Semin. Thorac. Cardiovasc. Surg.* 13, 301-19 (2001); Buckberg, et al. *J Thorac Cardiovasc Surg* 136, 578-89, 589 el-11 (2008); Ballester, et al. *Heart Fail. Clin.* 4, 261-72 (2008; Buckberg, et al. *Circulation.* 118, 2571-87 (2008)) was used to simplify the design and fabrication process of the soft robotic muscles. According to this theory, the ventricle of the heart can be unraveled into a singular muscular band that is spirally arranged in the three-dimensional space. A two dimensional ("2D") biomimetic matrix was constructed by embedding multiple linearly contracting pneumatic artificial muscles (PAMs) in a soft matrix based on the fiber orientations of the flat unraveled heart. Then, the soft robotic matrix is rewrapped into a 3D shape to recreate the hierarchical, functional architecture and the global, three-dimensional motion of the ventricular myocardium.

As represented in FIGS. 1A-1H, an explanted porcine heart is reconfigured so that the intact intracardiac structures (ex vivo endocardial scaffold) are preserved, but expired myocardial tissue is substituted with an actuatable HVMB-inspired synthetic myocardium to restore the dynamic motion of the beating heart. This dynamic heart model is referred to as a biorobotic hybrid heart.

A technological platform for creating an autonomously beating heart has been developed to overcome the current limitations in both synthetic manufacturing and tissue engineering. Existing biohybrid robots utilize living cells or tissues as actuators and synthetic materials passive structures (Ricotti, et al *Sci. Robot.* 2, eaaq0495 (2017); Webster-Wood et al. *Sci. Robot.* 2, eaap9281 (2017); and Park, et al. *Science.* 353, (2016)), but have limited scalability. To recreate the heart at the organ scale, techniques used in soft robotics were used to emulate complex biological motions, and to create organic tissue structures for accurate anatomical representation. The resulting biorobotic hybrid heart has accurate anatomical details, including valves, papillary muscles, moderator bands, chordae tendineae, vessels, and ventricular walls, and exhibits complex three-dimensional cardiac motion, a physiological level of contractile motion, and engagement of the interventricular septum, which presents an improvement over current passive models that are driven by internal or external pressure or flow.

Compared to ex vivo beating heart or in vivo animal hearts, the platform offers additional advantages with user flexibility and tunability. Since fixed tissues are utilized, all components in the heart model have longevity, allowing users to operate the heart on demand and perform repeated testing, with precise control of the motion of the heart. Cardiac parameters, such as heart rate, contractility, and stroke volume, can be tuned via an electropneumatic control system (Roche, et al. *Sci. Transl. Med.* 9, eaaf3925 (2017)) that controls individual actuators. This allows simulation of extreme conditions like exercise, or diseased conditions that may better represent the target patient population for intracardiac devices, such as heart failure (weaker actuation) or myocardial infarction (locally inactivated muscles). Furthermore, the soft robotic myocardium component may also be programmed to mimic a "patient-specific" cardiac fiber orientation and its resulting motion via in vivo DT-MRI (Nguyen, et al. *Magn. Reson. Med.* 76, 1354-63 (2016); Nguyen, et al. *JACC Basic to Transl. Sci.* 3, 97-109 (2018)).

In the development of the biorobotic hybrid heart, several technological hurdles had to be overcome:

First, a reliable adhesive interface between the synthetic and organic components in a wet, dynamic environment is required.

Since there were no commercially available adhesives for this application, a new silicone-based soft adhesive, referred to as "TISSUESIL," that has high adhesion strength, ability to tolerate physiological deformations without changing tissue mechanical properties, and function in wet environments. The adhesive allows conformable, flexible coupling of the tissue-silicone interface, which may be useful for future avenues in macroscale biohybrid robotics.

Second, inspired by the helical ventricular myocardial band theory, a simplified 2D design and fabrication strategies were used to make a functional 3D assembly, replicating the complex three-dimensional fiber architecture of cardiac muscles. In this process, DT-MRI was used to translate actual fiber architecture of cardiac tissues into an actuatable biomimetic matrix.

Third, a programmable, flat soft robotic matrix whose individual linear actuators can be oriented to match the cardiac tissue fibers was developed, and subsequently reconfigured into a 3D helix to represent the three-dimensional fiber architecture as well as the global cardiac motion. fPAMs generate lower contraction and higher radial expansion to native cardiomyocytes, resulting in an exaggerated myocardial wall thickening during the systolic phase.

The biorobotic hybrid heart has potential utility as a high-fidelity simulator for interventional cardiology applications, specifically involving minimally invasive procedures (such as self- or balloon-expanding valve prostheses or occluder devices). The overall vision of this work is to be able to recreate accurate patient-specific hemodynamics. DT-MRI is currently being performed on human patients in vivo. One could image a patient, create a patient-specific soft robotic model, test an intracardiac device in a mock circulatory loop with the biorobotic hybrid heart, for example, a prosthetic valve, and thus optimize its application to the patient, for example for reducing paravalvular leakage.

With a longer shelf-life and user controllability, this platform heart model allows faster evaluation and design iterations of intracardiac devices compared to in vivo testing. The model is compatible with various clinical imaging modalities, such as MRI, echocardiography and computed tomography. Medical device companies often offer training of their devices to interventional cardiologists, in which a portable, anthropomorphic, functional heart model, as presented here, would be beneficial. Overall, a robust model that can faithfully represent cardiac motion and preserve intracardiac organic structures is a valid alternative or supplement to animal testing for intracardiac device testing.

The present invention will be further understood by reference to the following non-limiting examples.

Construction of a BioHybrid Heart

FIGS. 2A-2L are schematics of the fabrication process for a passive biohybrid heart. FIGS. 2A-2D show casting of the outer mold: An explanted porcine heart (FIG. 2A) is preserved and the superior portion is placed in sulfur-free clay (FIG. 2B). The epicardial surface of the ventricular portion of the heart is then cast with MoldStar 15 (FIG. 2C) to yield the mold (FIG. 2D). FIGS. 2E-2H show the preserved heart dissected in a layer-wise fashion following the cardiomyocyte orientation in the left ventricle. FIGS. 21-2L show the passive biohybrid heart being cast by centering the dissected heart in the outer mold using supporting struts (FIG. 21). ECOFLEX® 00-20 is used for casting. Once cured, the assembly is demolded and disassembled (FIG. 2J). Next, tissue-silicone adhesive (TISSUESIL) is applied to the outer tissue surface (FIG. 2K) to yield the final product (FIG. 2L)

Ex Vivo Heart Casting of the Outer Mold

A freshly explanted porcine heart was obtained within 4 hours of sacrifice and thoroughly washed to remove excess blood and blood clots. Then, it was soaked in phosphate buffered saline at a 1 molar concentration (VWR) at 4° C. for 30 minutes to clear any remaining blood from the inside of the heart. Next, it was submerged in 10% formalin (Carolina Biological Supply) at room temperature for 3 days and subsequently rinsed with 1M phosphate buffered saline twice and stored in 4° C. An outer mold for the ventricular wall was cast prior to the dissection of the myocardial tissues. First, the fixed heart was positioned upside down with the atria and vessels anchored in sulfur-free clay (Smooth-On) in a custom-made acrylic box, leaving only the ventricular walls exposed. Next, silicone (Moldstar 15, Smooth-On) was poured into the assembly until the entire ventricle was covered, and then left to cure at room temperature for at least 5 hours. Subsequently, the box was disassembled, and the outer mold was obtained by detaching and removing the heart and clay. This casting serves as the outer mold for the final casting step of the biohybrid heart.

Ex Vivo Heart Dissection

The epicardial and myocardial tissue was removed by hand dissection. The outermost layer was removed following the fiber orientation. Next, starting at the right side of the anterior interventricular sulcus, which separates the right and left ventricle, the left ventricular free wall tissue was removed along the fiber orientation in a layer-by-layer manner until the transmurally changing fiber orientation became circumferential (or 0° to the base plane). This circumferential fiber direction indicated a continuum of the left ventricle in the interventricular septum and was used as a guide to separate the right ventricle from the left ventricle. The myocardial tissue of the left ventricle was trimmed until the fiber orientation became helical (60 degrees), which indicates that transmural depth has reached the endocardial layer. The right ventricular part of the interventricular septum was also further trimmed. This dissection process results in a heart with the endocardial layer and the intracardiac structures intact but without the myocardial tissues. Defects in the tissue created by the dissection process were repaired with a small amount of 2-octyl cyanoacrylate-based adhesive (KEG-500, Starbond) prior to the final molding step.

Casting of an Elastomeric Myocardial Shell

ECOFLEX® 00-20 (Smooth-On) was mixed at a 1:1 ratio (as indicated by the manufacturer) using a planetary centrifugal mixer (ARE-310, Thinky) for 30 s at 2000 rpm, followed by a degassing step for 30 s at 2200 rpm. Next, the mixture was placed in a vacuum chamber until air bubbles disappeared. The silicone was then poured into the outer mold, fabricated as described above. Next, endocardial heart tissue with the outer layers removed, as described above, was blotted dry with a Kimwipe on the outer, cut surface. The tissue was carefully placed in the outer mold in the uncured silicone. The atria and great vessels were covered with parafilm to prevent drying, and the assembly was cured at room temperature for 4 hours. The tissue was then removed from the elastomeric shell for subsequent adhesion at the tissue/elastomer interface.

Adhesion of Fixed Tissue and Elastomer

An adhesive containing the moiety:

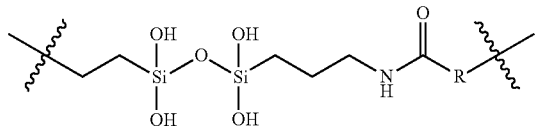

wherein, R is NH, O, or S, optionally wherein the termini are connected to a polymeric substrate (PDMS) or tissue was developed to adhere the synthetic and tissue components.

Polydimethylsiloxane (PDMS) (Sylgard 184, Dow Corning) was prepared by mixing the base and curing agents in a ratio of 20 to 1 using a planetary centrifugal mixer (ARE-310, Thinky) at 2000 rpm for 30 s followed by degassing at 2200 rpm for 30 s. Then, 1% (v/v) Triethoxyvinylsilane (Sigma) and 1% (v/v) 3-(Triethoxysilyl) propyl isocyanate (Sigma) were added and mixed in the same way. Finally, 0.8% (v/v) platinum catalyst (Sigma) was added and mixed in the final step to adjust the curing time needed to coat the surface. 40 g of this mixture was prepared for coating the surface of the endocardial tissue. The adhesive solution was applied onto the tissue surface using a high-density sponge along the fibers to minimize the formation of air bubbles. After assembling the tissue with pre-made silicone myocardium, it was left at room temperature for 20 min to cure and then stored in 4° C. overnight without mechanical disruption to allow coupling chemistry to occur prior to using the heart.

Figures 8, 9A, 9B, 9C:
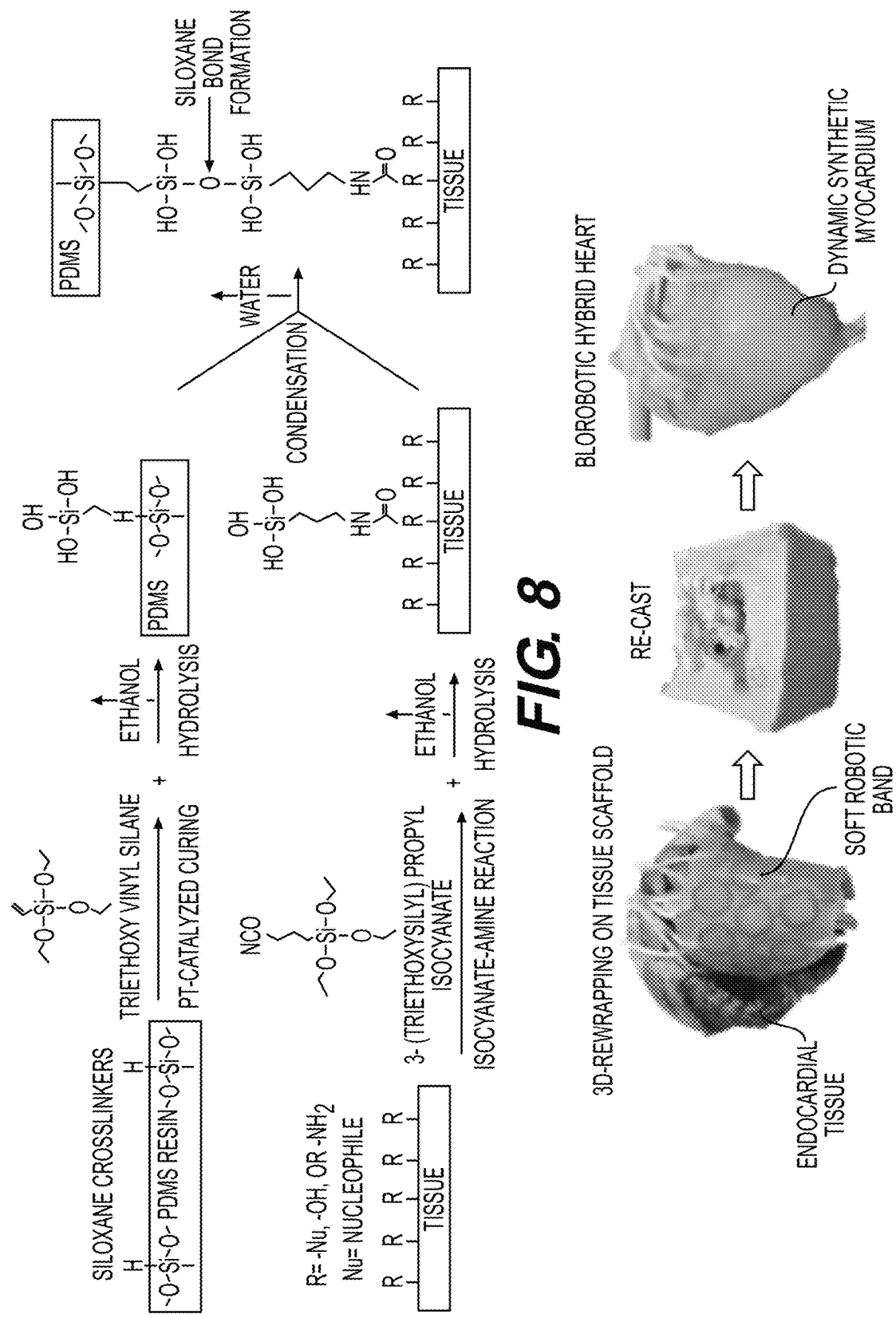
FIG. 8 shows the TISSUESIL bonding chemistry and penetration to microstructures.
FIGS. 9A-9C shows the assembly and construction of the biorobotic hybrid heart.

FIG. 8 shows the TISSUESIL bonding chemistry and penetration to microstructures.

A clear window of silicone/polymer in the ventricle/atria can be used for visualization of valve/device function and allow particle image velocimetry.

Mechanical Testing of Adhesive

Morphology of Cross-Sectioned TISSUESIL/Tissue Interface

TISSUESIL/swine myocardial tissue substrates were sectioned perpendicular to the adhesive plane, and freeze-dried for 12 hours. Scanning Electron Microscopic images were obtained by Zeiss Merlin High-resolution SEM at an acceleration voltage of 1 kV, and a working distance of 5-6 mm.

Adhesion Characterization of TISSUESIL Uniaxial Tensile Test

Laminates were evaluated with an Instron 5944 mechanical tester. Fixed tissue substrates of 3×2 sq. cm were cut using a ceramic knife. Next, a 0.5 mm thick layer of TISSUESIL, DURASEAL®, or Cyanoacrylate (CA) adhesive was spread evenly over the tissues (2 mm thickness). Once cured, the adhesive/tissue composites were loaded using mechanical vice style grips onto the mechanical fixture and uniaxially stretched at a rate of 10 mm min-1. TISSUESIL was mixed with SILPIG® (Smooth-On), and CA and DURASEAL® were mixed with dye (Indigotine and Fast green FCF) for better visual representation.

Figure 3A:
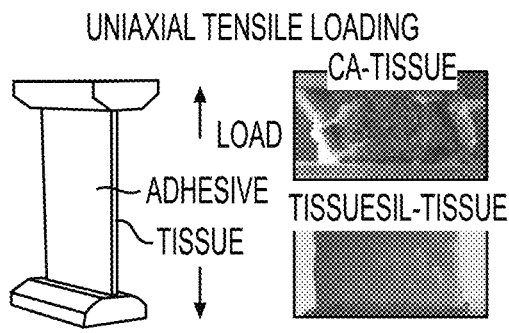
FIGS. 3A-3O are schematics of the mechanical characterization of adhesive/tissue interface and comparison to commercially available tissue adhesives. Test set-up (left, FIGS. 3A, 3D, 3G, 3J, 3M), representative data from each group tested (center, FIGS. 3B, 3E, 3H, 3K, 3N) and summary data (right, FIGS. 3C, 3F, 3I, 3L, 3O).
Figure 3B:
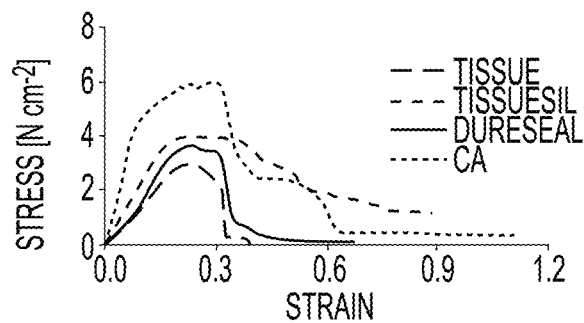
Figure 3C:
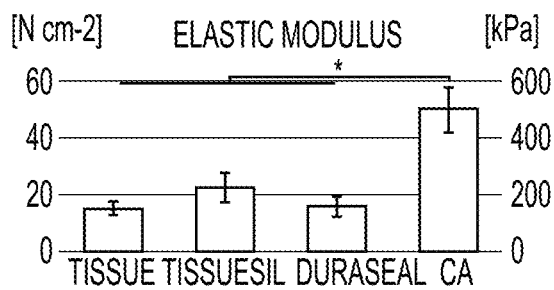
Figure 3D:
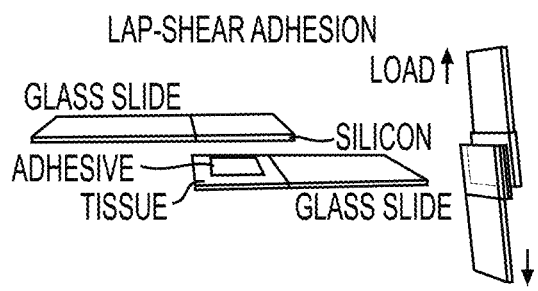
FIGS. 3D-3F shows testing and results of the Lap-shear adhesion test.
Figure 3E:
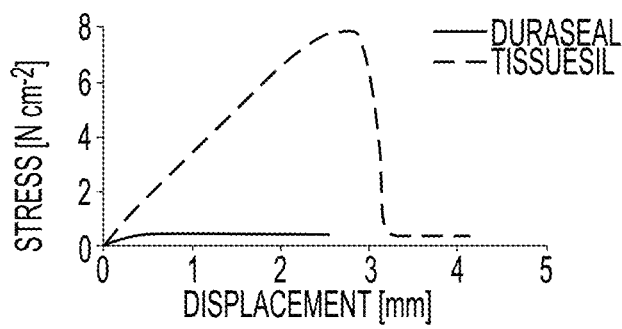
Figure 3F:
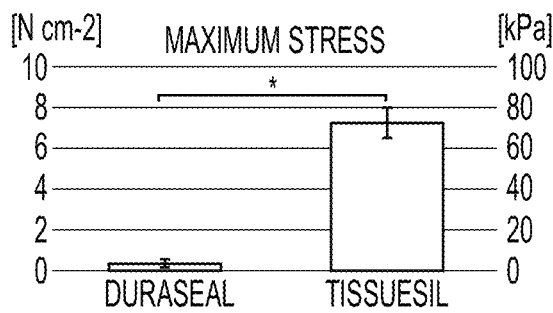
Figure 3G:
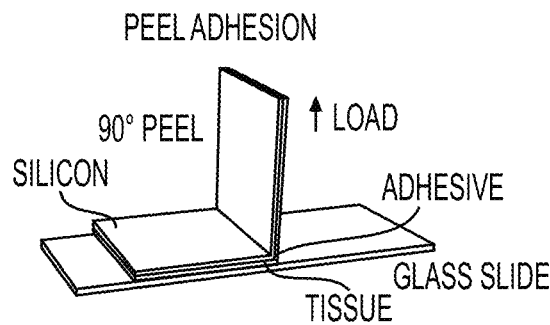
FIGS. 3G-3I show testing and results of the 90-degree peel test.
Figure 3H:
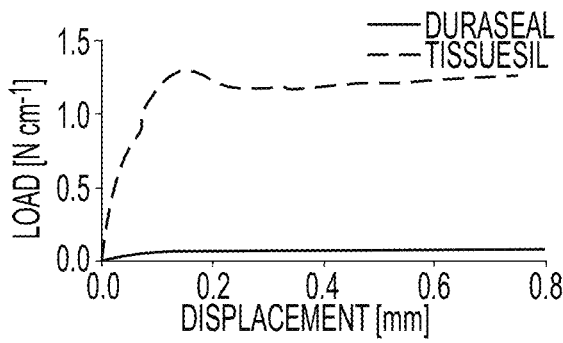
Figure 3I:
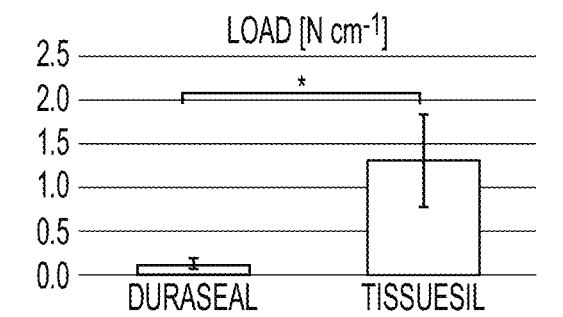
Figure 3J:
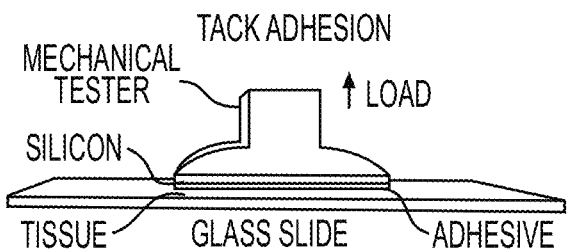
FIGS. 3J-3L shows tack adhesion testing.
Figure 3K:
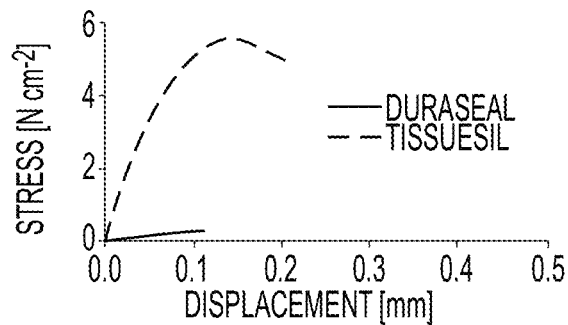
Figure 3L:
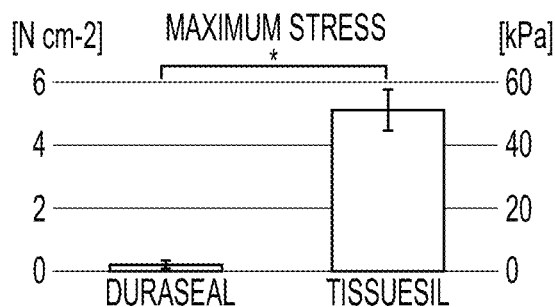
Figure 3M:
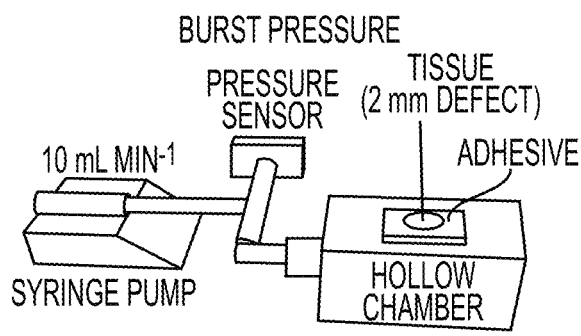
Figure 3N:
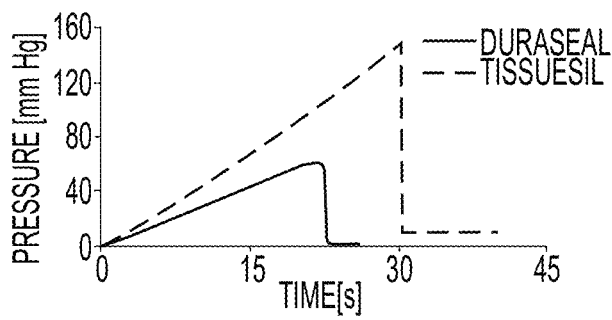
Figure 3O:
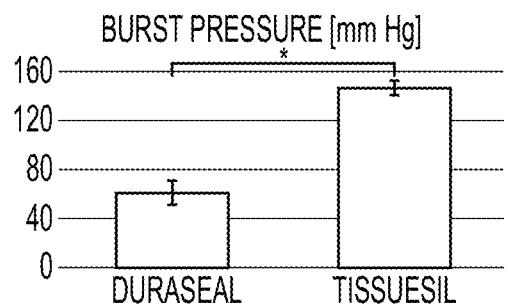

FIGS. 3A-3O are schematics of the mechanical characterization of adhesive/tissue interface and comparison to commercially available tissue adhesives. Test set-up (left, FIGS. 3A, 3D, 3G, 3J, 3M), representative data from each group tested (center, FIGS. 3B, 3E, 3H, 3N) and summary data (right, FIGS. 3C, 3F, 3I, 3O). FIGS. 3A-3C shows Uniaxial tensile testing of samples of tissue coated with adhesive. Inset in FIG. 3A shows cracking of cyanoacrylate (CA) and co-stretching of TISSUESIL during tensile loading. FIGS. 3D-3F shows testing and results of the Lap-shear adhesion test. FIGS. 3G-3I show testing and results of the 90-degree peel test. FIGS. 3J-3L shows tack adhesion testing. FIGS. 3M-3O shows burst pressure testing.

Lap Shear Strength

Maximum lap shear at failure was measured according to a modified ASTM F2255-05 protocol. Fixed myocardium tissue sections (2×2 sq. cm) and silicone (ECOFLEX®) sheets were adhered on microscopic glass slides using LOCTITE® 422 and SIL-PDXY® adhesives, respectively. A 0.3 mm thick layer of adhesive was sandwiched between the silicone sheet and myocardium tissue. TISSUESIL, DuraSeal®, and CA adhesives were cured for 12 hrs, 2 min, and 5 min, respectively. Lap shear failure was quantified by a mechanical tensile tester fixed with a 2 kN load cell (Instron 5944), with a linear extension of 3 mm min-1.

Peel Strength

Peel strength was quantified according to a modified ASTM D6862-11 protocol. Fixed myocardial tissue sections (2×2 sq. cm) were adhered on microscopic glass slides using Loctite 422 Cyanoacrylate adhesive. A silicone sheet (7×2.5 sq. cm) was adhered on the myocardium tissue substrates using TISSUESIL®, DURASEAL®, and CA adhesives. A 90-degree peel test was conducted using a 5944 Instron mechanical tensile tester and maximum force at delamination was recorded by elongating at a rate of 3 mm min-1.

Figure 11:
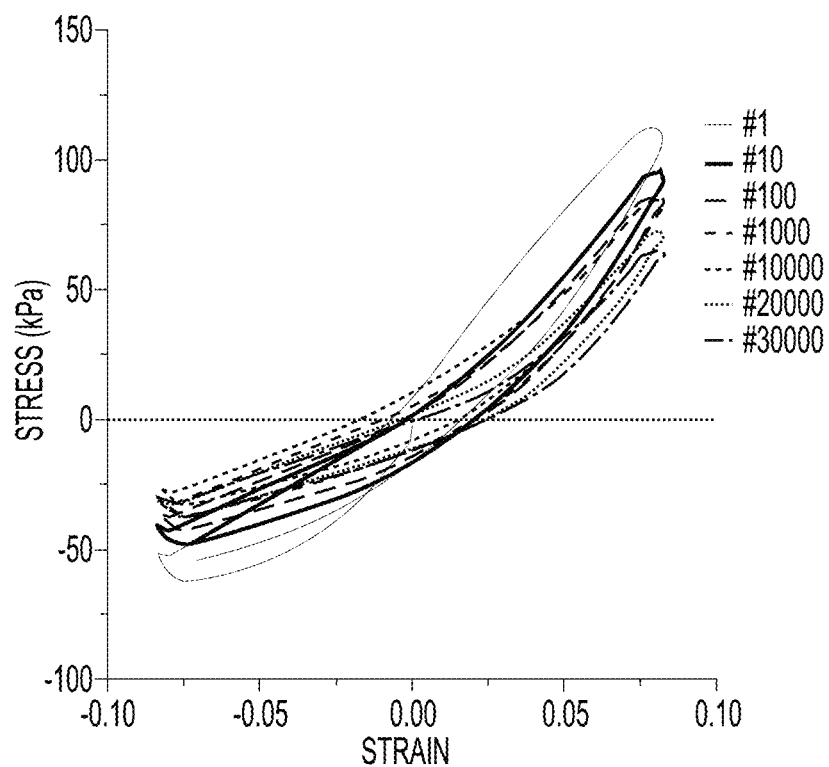
FIG. 11 is a graph of cyclic fatigue testing on fixed tissue-adhesive composite. Tension-compression cyclic strain loading of +/−1.66 mm (or 8.3%) at 1 Hz up to 30,000 cycles of triangular waveforms under ambient temperature. The test was started with a small area of delamination, 2.4% of total bonding area (N=0) to 4.5% (N>100). The delamination area was approximately 16.3% when the test was terminated (N>30,000). Tissue-cyanoacrylate showed immediate adhesive failure at the 1st cycle.

FIG. 11 is a graph of cyclic fatigue testing on fixed tissue-adhesive composite. Tension-compression cyclic strain loading of +/−1.66 mm (or 8.3%) at 1 Hz up to 30,000 cycles of triangular waveforms under ambient temperature. The test was started with a small area of delamination, 2.4% of total bonding area (N=0) to 4.5% (N>100). The delamination area was approximately 16.3% when the test was terminated (N>30,000). Tissue-cyanoacrylate showed immediate adhesive failure at the 1st cycle.

Tack Adhesion

Fixed myocardium tissue sections (2×2 sq. cm) and silicone (ECOFLEX®) sheets were adhered on microscopic glass slides using LOCTITE® 422 and SIL-PDXY® adhesives, respectively. A thin layer (0.3 mm) of the adhesive was applied between the myocardium tissue and silicone sections. The pull-off strength was measured using a 5944 INSTRON® mechanical tester at an elongation rate of 3 mm min-1. Silicone sheet detachment from the tissue surface was quantified as the maximum load before failure.

Burst Pressure

The hydraulic burst pressure was performed according to a modified ASTM F2392-04 protocol. Fixed porcine myocardium tissues were cut to a dimension of 2×2 sq. cm and a 2 mm defect was created at the center using a 13-gauge needle. A syringe pump was connected to the pressure sensor and a 1.5 mL hollow chamber using a T-connector. The upper piece of the hollow chamber had a 10-mm-diameter opening, and tissue substrates were placed over it and secured using a flange. A 0.3 mm layer of adhesive was spread over the defect. Air (10 mL min-1) was inserted into the cavity, and burst pressure was recorded via the pressure sensor (Truwave, Edwards Life Sciences).

MicroCT Imaging of the Adhesive Conformability

The conformation of TISSUESIL (10% barium sulfate as a contrast agent) to the heart tissue and synthetic myocardium was visualized by means of micro-computed tomography (micro-CT) with an X-Tek XRA-002 microCT system (Nikon Metrology Inc., Brighton, MI). The 3D reconstructions were performed using CT-Pro (Nikon Metrology Inc., Brighton, MI) and surface renderings were generated using VGStudio Max (Volume Graphics GmbH, Heidelberg, Germany).

Characterization of Actuators

For linear contraction and radial displacement characterization, the actuator specimens were dynamically actuated for 300 ms at 60 bpm using a custom electropneumatic control system. All specimens were marked with optical trackers and the motion was video recorded at 60 fps. Screenshot images of the specimens were analyzed by tracking the relative displacements of optical markers and quantified using a MATLAB script. Dynamic force was measured for actuator specimens using a mechanical tester (INSTRON® 5944). The specimens were held at a fixed position and dynamically actuated for 300 ms at 60 bpm to record the force. The peak force was calculated and averaged over 10 peaks for analysis. For area reduction characterization, circumferential actuator specimens were dynamically actuated and video recorded as before. The screenshots were processed using an image processing tool (ImageJ) to calculate the change in the inner area of the actuators.

Figure 5G:
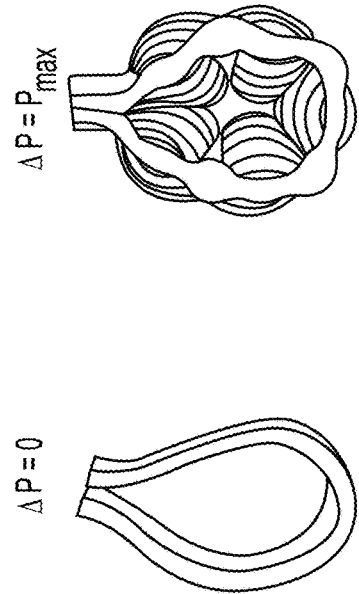
Figures 5H, 5I:
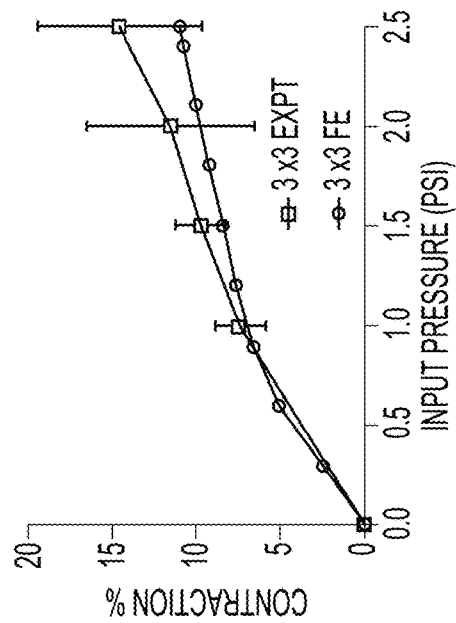
Figure 5J:
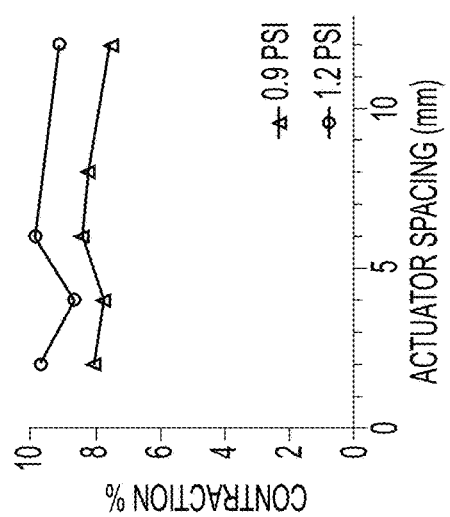
Figure 5K:
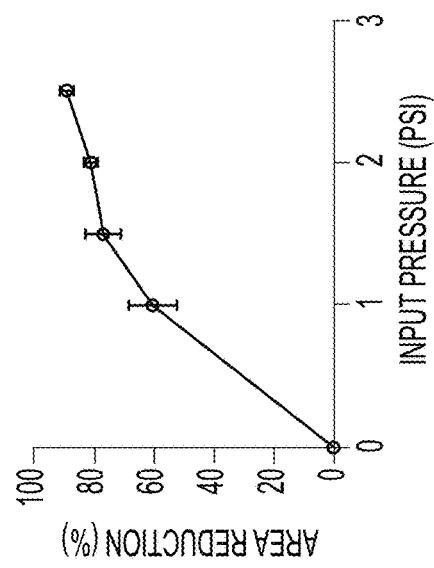

FIGS. 5A-5J are the characterization of multiple-array matrices of soft robotic cardiac muscles. FIGS. 5A and 5B are graphs of the FE prediction of contraction percentage and force generation of serial arrays (1×1, 2×1, 3×1). FIGS. 5C and 5D are graphs of the modeling of contraction percentage (1×1, 1×2 and 1×3) and force generation (3×1, 3×2, 3×3) of parallel arrays. FIGS. 5E and 5F show the contraction of a 3×3 array experimentally (FIG. 5E) and computationally FIG. 5F) at ΔPmax. The contour plot shows Mises stresses in the FE simulation. The graph shows percentage contraction at different input pressures (bottom). FIG. 5G is a graph of the FE prediction of contraction for different actuator spacing in an array. FIGS. 5H and 5I show the inner area reduction of a circumferentially oriented single array with increasing pressure. FIG. 5J is a graph of the uninflated and FIG. 5K is a graph of the inflated state at ΔPmax. ΔPmax=2.5 psi. Data are mean±S.D. n=3.

Finite Element Modeling of the Actuators

ABAQUS/Standard 2017 (Dassault Systèmes, Vélizy-Villacoublay, France) was used to calculate the quasi-static solution of the finite element model in order to predict linear contraction, radial expansion and generated force as well as to optimize the actuator design. ECOFLEX® 00-20 silicone was modeled as hyperelastic and isotropic material using a three-term Ogden strain energy potential material model ($\mu 1$=0.005954916846 N mm-2; $\mu 2$=0.002746417247 N mm-2; $\mu 3$=0.00905891419 N mm-2; $\alpha 1$=3.98529341; $\alpha 2$=2.47960094; $\alpha 3$=−3.58683068; D1=D2=D3=0 (N mm-2)-1) and 10-node quadratic tetrahedron solid elements with a hybrid formulation (C3D10H). The hyperelastic properties were determined with an Instron 5944 universal testing system using the uniaxial tensile testing procedure according to the ASTM 412 standard (specimen design: type C; number of samples: n=5). 3D linear quad-dominated shell elements (S4R) with reduced integration were used to model the very thin paper pleats. In a uniaxial tensile test (ASTM D828; number of samples:

n=8) linear elastic material behavior of the 45% polyester-55% cellulose blend paper was derived for small strains (<3%) corresponding to the strains identified in the simulated shell elements. A Young's modulus of 120 MPa was derived from the slope along the experimentally found nominal stress/strain curve. For the incompressible material, a Poisson's ratio of 0.499 was chosen.

The accuracy of the mesh was ascertained through a mesh refinement study, resulting in mesh seedings of 0.9 mm for the silicone matrix and 0.6 mm for the shell elements of the strain-limiting layer. To avoid extensive distortion of elements along the very thin air cavities (300 µm), the mesh was refined to a seeding size of 0.4 mm in those areas. The interaction between the two material structures was simplified by fixing the shell elements of the paper (slave) to the outer surface of the silicone (master) using tie constraints. As boundary conditions, elements on one of the end faces of the actuator were fixed in all six degrees of freedom to measure the maximal linear and radial displacement. In order to derive the generated force of an actuator, these boundary conditions were applied to nodes on both ends. A uniformly distributed linear pressure with a magnitude of 3 psi was applied to the surfaces of the air cavities over an equally spaced time frame of one second with an initial time increment of 0.01 s.

Figure 10:
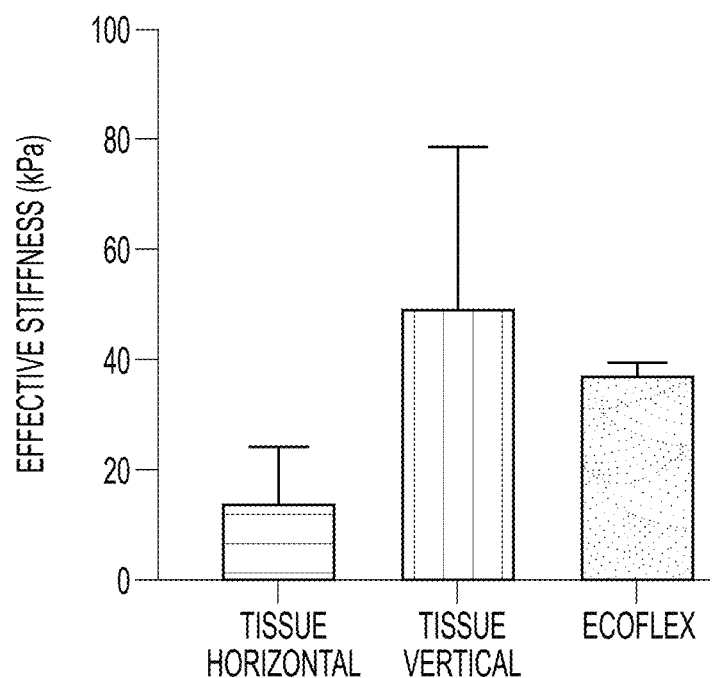
FIG. 10 is a graph of the uniaxial tensile testing of fresh versus synthetic myocardium. Effective stiffness of synthetic myocardium made out of a soft elastomeric matrix, ECO-FLEX® 00-20, is compared to fresh myocardial tissue stretched across (horizontal) and along (vertical) the fiber direction.

FIG. 10 is a graph of the uniaxial tensile testing of fresh versus synthetic myocardium. Effective stiffness of synthetic myocardium made out of a soft elastomeric matrix, ECOFLEX® 00-20, is compared to fresh myocardial tissue stretched across (horizontal) and along (vertical) the fiber direction.

Helical Ventricular Myocardial Band

A helical ventricular myocardial band can be prepared using a method such as the following exemplary method, using fresh explanted heart tissue or chemically preserved heart tissue.

A freshly explanted porcine heart is dissected following Torrent-Guasp's simple hand dissection method. The heart is first boiled in water for about 20 min to soften the tissue. The vessels and atria are removed, so that only the ventricular myocardial tissue remained. First, the right ventricular tissue is separated by dissection starting from the left side of the anterior interventricular sulcus, detaching the pulmonary artery. At the posterior limit of the right ventricular cavity, where the free right ventricular wall meets the septum, the cleavage plane is dissected all the way to the aorta. The descending fibers are separated from the superficial layers. Next, the cleavage plane is identified in the septum by the sudden change in the fiber orientations from horizontal to vertical directions. The layers are separated along the natural fiber directions. The aorta is separated from the rest of the heart by cutting the right fibrous trigone. The entire structure is unraveled into a single ventricular myocardial band.

Fabrication of the Soft Robotic Myocardial Band

The following exemplary method shows how the soft robotic myocardial band can be constructed.

Sheets of ECOFLEX® 00-20 of 1.2 mm thickness are pre-fabricated by depositing prepolymer solution using a silicone applicator, followed by curing at room temperature for about 1.5 hr. The paper pleat layer is made using a material such as wiper papers (polyester/cellulose blend paper, VWR), and the air chambers can be formed using a water-soluble such as polyvinyl alcohol (PVA) mask (ULTRASOLVY® stabilizer, Sulky). Both paper pleats and water-soluble mask are laser cut in defined geometries.

Prior to assembly, the paper layer is wet with about 40 g of uncured ECOFLEX® 00-20 prepolymer liquid, or a comparable polymer, and degassed to ensure proper integration of paper and elastomer. Then, PVA is sandwiched between two paper pleat sheets for the inner layers and two silicone sheets on the outer layers, and bonded using uncured ECOFLEX® 00-20. A flat plate can be used to apply even pressure on top of the assembly to form a good seal. The assembly is cured in the oven at 60° C. for 20 min or room temperature about an hour. Once cured, the actuator is trimmed, for example, with scissors, and injected with water to dissolve the PVA layer and left at room temperature for about an hour. PVA gel is ejected by rolling a rod on the actuator body. This process is repeated two times. Air supply tubings (⅛" OD silicone tubing, McMaster) are inserted to the ports by pre-inserting a 1/16" metal rod and then sliding a silicone tubing over, and then using a material such as SIL-PDXY® (Smooth-On) to seal the two materials.

Assembly and Actuation of the Biorobotic Hybrid Heart

The biorobotic hybrid heart is assembled by wrapping flat soft robotic bands around the left ventricular endocardial tissue and casting an elastomer such as silicone matrix following the outer ventricular wall geometry using an outer wall mold. The DTI-inspired synthetic band is bonded to the tissue starting with the descending segment ends at the posterior side of the left ventricle and ending with the ascending segments placed in the septal space to mimic the left ventricular helicoid. In a preferred embodiment, the endocardial tissue is precoated with TISSUESIL as described above and left overnight to complete the reaction chemistry. Pre-polymer solution of ECOFLEX® 00-20 (SmoothOn) was used as an adhesive to bond between the bands and to the tissue surface, and 0.1% platinum catalyst (Sigma) was added to the uncured ECOFLEX® solution to accelerate the bonding process to about 5 min at room temperature. Prior to casting the outer wall, pliable metal wires are inserted through the air supply tubings to prevent blockage of the airway during the molding process and pulled out after casting. The ECOFLEX® 00-20 is poured between the tissue-band assembly and outer wall, and placed in a vacuum chamber while curing to remove air bubbles in the final construct. After curing at room temperature for two hours, the outer mold is demolded. The biorobotic hybrid heart is actuated using an electropneumatic control system and 400 ms at 40 Hz used for the MRI motion study.

Characterization and Testing of Biohybrid Heart
Magnetic Resonance Imaging of Biorobotic Hybrid Heart Retrospective steady-state gradient recall echo (GRE) cinematographic (CINE) MRI (TR=5.1, TE=1.4, flip angle=12 degrees, 1×1×6 mm3, 24 frames per heartbeat) was performed on a 3T clinical scanner (Connectome, Siemens Healthineers, Erlangen, Germany) and synced to the 40 Hz pneumatic actuator pumps. CINE GRE MRI was performed over 5 actuator cycles to reconstruct a high-resolution 2D section and repeated to cover the entire heart. 3D high-resolution structural GRE MRI (TR=5.1, TE=1.4, flip angle=12 degrees, 1 mm isotropic resolution) was performed to identify actuators, silicone myocardium, and ventricular chamber.

Echocardiography 2D and 3D echocardiography of an in vivo porcine heart and the biorobotic hybrid heart was performed by a cardiologist using an iE33 ultrasound machine (Phillips) with an x7-2 transducer probe (Phillips). For quantitative analysis, a long-axis view was used to make a comparison since the short-axis view can be inaccurate due to irregular inner chamber geometry. Area reduction was determined from the end-diastolic and end-systolic images of 2D echocardiography. Ejection fraction was determined from the same images using a single-plane long-axis area-length method. Systolic and diastolic LV area and length was determined in an image processing software (ImageJ) based on manual segmentation of the left ventricle chamber. Short-axis images/movies were obtained from 3D echocardiography using QLAB software (Phillips).

Figure 12:
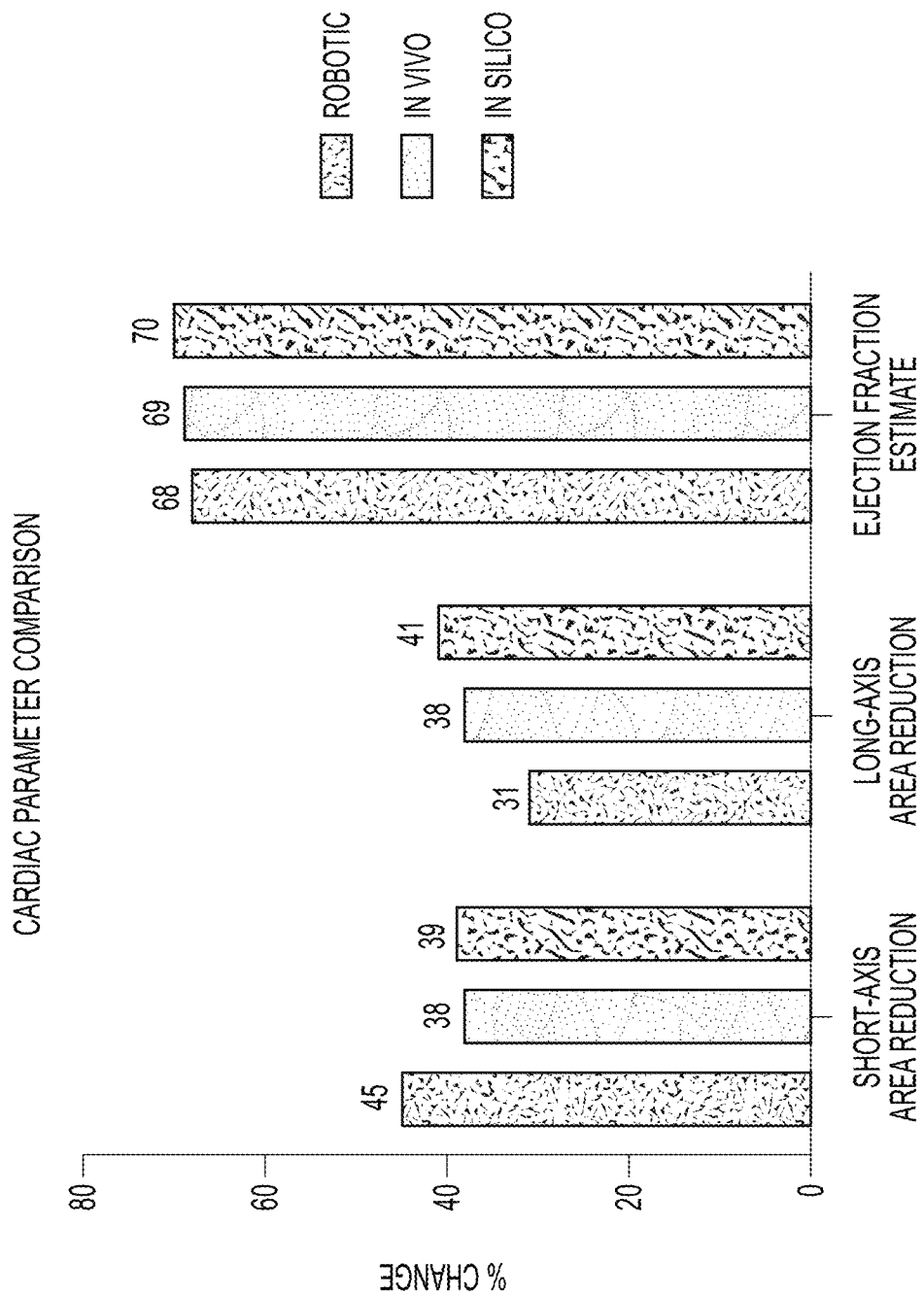
FIG. 12 is a graph of the cardiac parameter comparison of the biorobotic hybrid heart model to existing heart models. Area reduction in the short-axis plane (left), area reduction in the long-axis plane (center), and estimated ejection fraction (right) for the biorobotic hybrid heart (pink) and in vivo porcine heart (orange) motion under echocardiography, and the predicted motion from the in silico DTI-FE model (olive green).

FIG. 12 is a graph of the cardiac parameter comparison of the biorobotic hybrid heart model to existing heart models. Area reduction in the short-axis plane (left), area reduction in the long-axis plane (center), and estimated ejection fraction (right) for the biorobotic hybrid heart (pink) and in vivo porcine heart (orange) motion under echocardiography, and the predicted motion from the in silico DTI-FE model (olive green).

Imaging and Post-Processing of Fiber Orientation, Finite Element Modeling of the Left Ventricle The fiber orientation of both the 2D myocardial tissue band and the 3D intact heart were imaged with DT-MRI (3D multi-shot spin echo planar imaging, TR=2500 ms, TE=45 ms, 1 mm isotropic spatial resolution, 5 shots, b-value=0, 500 s/mm2, and 12 directions) using a Siemens Connectome 3T scanner (Siemens Healthineers, Erlangen, Germany). For the 2D myocardial band, the left ventricular portion of the band was isolated. The vector field that indicates the fiber structure was created by obtaining the primary eigenvector of the 3×3 diffusion gradient matrix in each voxel. The data points for the subepicardial surface were extracted and all associated vectors and the surface contour were projected to a 2D plane. This provided the contour shape of the soft-robotic band. Fiber tractography was conducted to interpret the dense vector field into several continuous fiber tracts. The original vector field was also simplified by partitioning the entire band using a 10×10 mm grid and assigning the corresponding region-averaged vector to each square in the grid. The fiber tractography and the coarse vector field were used to guide the design of the actuator patterns. All post-processing was conducted using MATLAB (The MathWorks, Inc., Natick, MA, USA). A similar method was used to process DT-MRI data of the 3D intact heart. The MRI geometry and the DTI fiber structure were converted into Abaqus creating a subject-specific finite element model of the left ventricle.

Statistical Analysis

All data are presented as mean±SD (n=3 for adhesion testing). Significance (p<0.05) was assessed by a t-test for comparisons between two groups and with a one-way ANOVA with Tukey post-hoc correction for comparison between more than two groups. OriginPro 2019 64-bit Software was used for statistical analysis.

Results

Design and Construction of a Bioinspired Soft Robotic Myocardial Band

Inspired by the left ventricular portion of the helical ventricular myocardial band, a soft robotic myocardium was constructed. See FIGS. 6A-6F. The unraveling of the heart into the ventricular myocardial band is shown in FIGS. 6A-6D. FIGS. 7A-7I depict how diffusion tensor magnetic resonance imaging (DT-MRI) was used to identify the directions of greatest diffusion in tissue, corresponding to the cardiomyocyte orientation of the band. This imaging technique enabled replication of the fine myocardial structure with an active synthetic substitute. First, the apical loop of the unraveled band (ascending and descending segments) were scanned with DT-MRI. Using a MATLAB script, the sub-epicardial surface and outer contour of the heart were located. Then the DTI data was projected on a 2D plane, and tractography performed to visualize the cardiac myofiber directions. Next, a coarser grid containing the principal diffusion directions was generated. Based on these two datasets, a soft robotic myocardial band was designed with an array of actuators following the fiber orientations of the unraveled band in a computer-aided design package (Solidworks). The 2D soft robotic myocardial band was generated.

Assembly, Actuation, Imaging of the Biorobotic Hybrid Heart and Comparison to In Vivo and in Silico Heart Models FIGS. 9A-9C shows the assembly and construction of the biorobotic hybrid heart. The soft robotic myocardial band was wrapped in a 3D helical fashion around the left ventricular and the interventricular septal endocardial tissue from a dissected, preserved porcine heart with intact intracardiac structures. Next, this tissue/soft robotic band assembly was supported in the outer mold, and any remaining space between them was cast with ECOFLEX® 00-20 (see 'Assembly and actuation of the biorobotic hybrid heart' in Materials and Methods), the same material as the soft robotic myocardial band resulting in seamless integration with the actuators. The resulting biorobotic hybrid heart had an actuatable myocardial wall, with minimal actuator air cavity in the deflated state, and intact endocardial structures that could be imaged with an endoscopic camera.

Figure 4B:
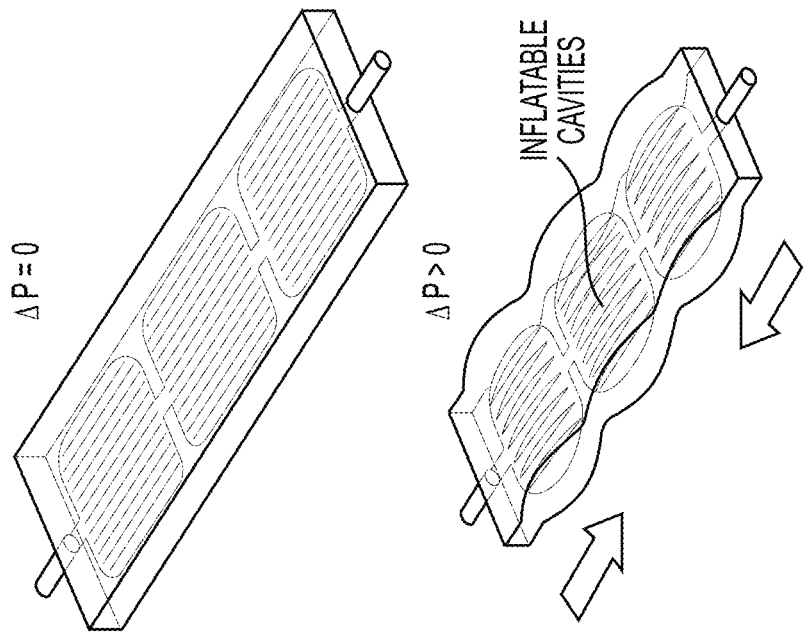
Figure 4A:
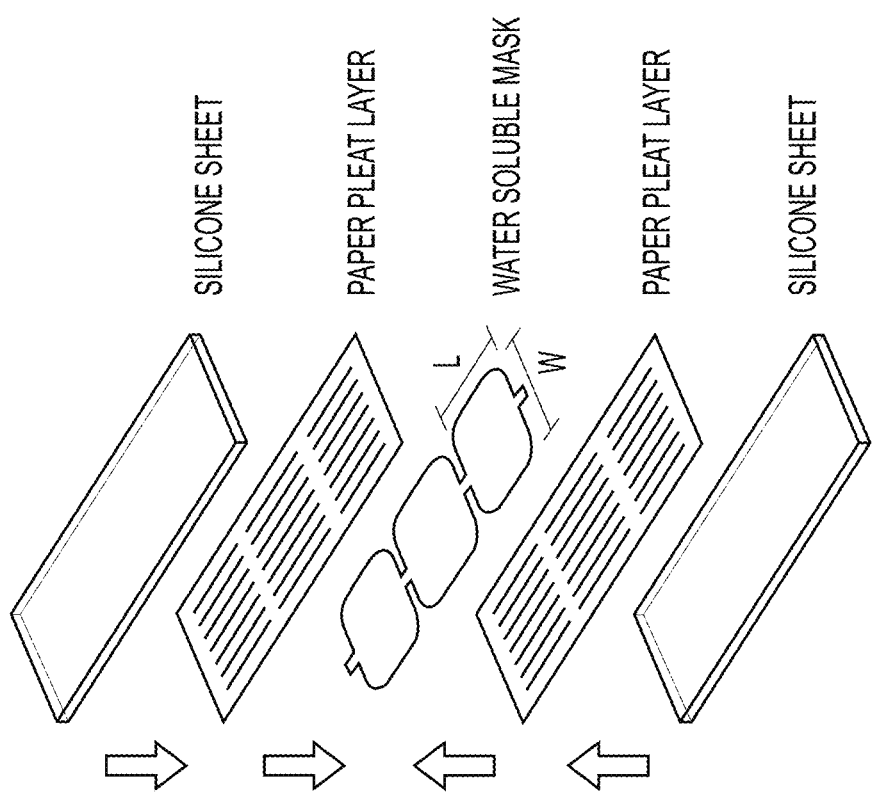

FIGS. 4A-4J shows the fabrication and mechanical and computational characterization of single-array fPAMs. FIGS. 4A and 4B show the fabrication process for fPAMs. FIGS. 4C-4E shows a comparison of linear contraction (n=5 for 20 mm×20 mm, n=4 for 14 mm×14 mm) and FIGS. 4F-4H show the radial displacement (n=3) measured experimentally and predicted computationally at P=ΔPmax. FIG. 4I is a graph of the force generation for increasing input pressures measured experimentally (n=6) and predicted computationally. FIG. 4J is a graph of the computational prediction of percentage linear contraction for various aspect ratios (L/W). Data are mean±S.D. L=length of bladder, W=width of bladder, P=actuation input pressure. ΔPmax=2.5 psi. FE=finite element.

The biorobotic hybrid heart was actuated while performing 4D MRI to observe whether the soft robotic myocardium and organic endocardium are coupled. With MRI, the movement of the ventricular walls can be visualized as the fPAMs inflate and deflate, and the conformability of the synthetic myocardium to the endocardial tissue throughout the cardiac cycle. The left ventricular chamber showed reduction and wall thickening between the end of the filling cycle (end-diastole, where the internal pressure of the fPAMs is zero) and end of the ejection cycle (end-systole, where the internal pressure of the fPAMs is positive). Notably, the interventricular septum is engaged in this movement, and moves as a part of the left ventricle, which is difficult to achieve with existing flow-driven benchtop models.

The contractile motion of the biorobotic hybrid heart was evaluated and compared to an in vivo and in silico healthy. Echocardiography of the healthy porcine heart was acquired prior to explant. After the heart was explanted, DT-MRI scanning of the intact heart was conducted, and this data used to construct a dynamic FE model based on its 3D geometry and fiber orientation. A similar chamber size reduction in the biorobotic hybrid heart compared to its corresponding in vivo and in silico models in both the short- and long-axis view was observed. The ejection fraction from the biorobotic hybrid heart is 68%, showing an excellent agreement with both in vivo and in silico models, which had ejection fraction of 69% and 70%, respectively. These values are within expected physiological range.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A biohybrid heart comprising
organic endocardial tissue scaffold comprising one or more intact intracardiac structures from an explanted heart, and
synthetic myocardium,
wherein the endocardial tissue scaffold and synthetic myocardium is combined to form an explanted heart with myocardial tissue and one or more intact intracardiac structures and passive or active synthetic myocardium.

2. The heart of claim 1 comprising endocardial tissue selected from the group consisting of heart valve leaflets, and heart chordae.

3. The heart of claim 1 functioning as a biorobotic hybrid heart with accurate anatomical details, comprising valves, papillary muscles, moderator bands, chordae tendineae, vessels, and ventricular walls.

4. The heart of claim 1 exhibiting complex three-dimensional cardiac motion and a physiological level of contractile motion.

5. The heart of claim 4 exhibiting complex three-dimensional cardiac motion, a physiological level of contractile motion, and engagement of the interventricular septum.

6. The heart of claim 1 comprising synthetic myocardium exhibiting three-dimensional contraction resulting in the reduction of one or more chamber volumes.

7. The heart of claim 1 having physiological hemodynamic performance.

8. The heart of claim 1 comprising organic myocardial tissue removed or separated from endocardial tissue.

9. The heart of claim 1, wherein the synthetic myocardium is passive.

10. The heart of claim 9, wherein the synthetic myocardium is formed of a soft silicone elastomer.

11. The heart of claim 1, wherein the synthetic myocardium is active.

12. The heart of claim 11, wherein the active synthetic myocardium drives the motion of the heart.

13. The heart of claim 1 wherein the endocardial tissue scaffold is unfolded from the entire ventricular myocardial tissue.

14. The heart of claim 1 comprising individual soft robotic actuators in the synthetic myocardium to create cardiac motion.

15. The heart of claim 1 wherein the endocardial tissue scaffold is adhered to the synthetic myocardium to form a soft, flexible, conformable, and watertight organosynthetic interface.

16. The heart of claim 1 comprising an array of programmable linearly contracting soft robotic actuators to mimic the native heart anisotropy.

17. The heart of claim 16 comprising an array of programmable linearly contracting soft robotic actuators formed by molding, casting or three dimensional printing.

18. The heart of claim 16 wherein the actuators are soft actuators.

19. The heart of claim 16 comprising flat pleated pneumatic artificial muscles comprising orientable fine fiber reinforcement to mimic the native heart tissue anisotropy.

20. The heart of claim 1 having accurate anatomical details, including valves, papillary muscles, moderator bands, chordae tendineae, vessels, and ventricular walls, and exhibiting complex three-dimensional cardiac motion, a physiological level of contractile motion, and engagement of the interventricular septum.

21. The heart of claim 1 comprising a programmable, soft robotic matrix comprising orientable actuators to mimic the cardiac tissue fibers of the native myocardium.

22. The heart of claim 1 comprising an electropneumatic control system.

23. The heart of claim 1 wherein the adhesive has the structure

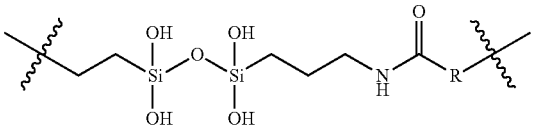

wherein, R is NH, O, or S, optionally wherein the termini are connected to a polymeric substrate substrate or tissue.

24. The biohybrid heart of claim 1 wherein the endocardial tissue scaffold and synthetic myocardium is combined to form an explanted heart with myocardial tissue and one or more intact intracardiac structures and passive and active synthetic myocardium.

25. A method of making a biorobotic hybrid heart comprising
combining an organic endocardial tissue scaffold comprising one or more intact intracardiac structures from an explanted heart and synthetic myocardium.

26. The method of claim 25 comprising
providing organic endocardial tissue from a preserved explanted heart with intact intracardiac structures and without myocardial tissue,
providing explanted heart tissue that is dissected and unraveled to form a flat, helical ventricular myocardial band,
using diffusion tensor magnetic resonance imaging of the intact and unraveled heart to guide the development of a synthetic myocardial substitute,
forming the synthetic myocardial substitute,
rewrapping the flat, helical ventricular myocardial band in the synthetic mycocardial band and
adhering the organic and synthetic structures together to form a biorobotic hybrid heart.

27. The method of claim 26 comprising incorporating into the synthetic myocardium individual soft robotic actuators formed using molding, casting or three dimensional printing.

28. The method of claim 26 comprising incorporating into the heart an array of flat pleated soft pneumatic artificial muscle whose fine fiber reinforcement is orientable to mimic the native heart tissue anisotropy.

29. The method of claim 26 comprising incorporating into the synthetic myocardium individual soft robotic actuators to create cardiac motion.

30. The method of claim 26 comprising incorporating into the heart an array of soft pneumatic artificial muscle.

31. The method of claim 26 wherein the endocardial tissue scaffold is made from tissue, from decellularized tissue, from biopolymers, or 3D printed scaffolds.

32. The method of claim 26 comprising providing a programmable, soft robotic matrix comprising orientable linear actuators to mimic the cardiac tissue fibers of the organic myocardial tissue.

33. The method of claim 26 comprising providing an electropneumatic control system.

34. The heart of claim 1 comprising endocardial tissue selected from the group consisting of heart valve leaflets, heart chordae from an explanted heart and intracardiac components formed of synthetic materials.

* * * * *